United States Patent
Ito et al.

(10) Patent No.: US 7,247,757 B2
(45) Date of Patent: Jul. 24, 2007

(54) METHOD OF PRODUCING A FLUORINE-CONTAINING VINYL ETHER COMPOUND

(75) Inventors: Takayuki Ito, Minami-ashigara (JP); Yushi Kaneko, Minami-ashigara (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/242,801

(22) Filed: Oct. 5, 2005

(65) Prior Publication Data

US 2006/0074264 A1   Apr. 6, 2006

(51) Int. Cl.
*C07C 41/24* (2006.01)
*C07C 43/172* (2006.01)

(52) U.S. Cl. .................. 568/683; 568/684; 568/685

(58) Field of Classification Search ............. 568/683, 568/684, 685
See application file for complete search history.

(56) References Cited

U.S. PATENT DOCUMENTS 5,350,497 A    9/1994 Hung et al.

FOREIGN PATENT DOCUMENTS

EP    0 201 871 A1    11/1986
JP    2003-508374 A    3/2003
JP    2005-68044 A    3/2005
WO    WO-02/20445 A1    3/2002

*Primary Examiner*—Rosalynd Keys
(74) *Attorney, Agent, or Firm*—Birch, Stewart, Kolasch & Birch, LLP

(57) ABSTRACT

A method of producing a fluorine-containing vinyl ether compound, which contains the step of: fluorinating a compound of formula (I-1) or (I-2):

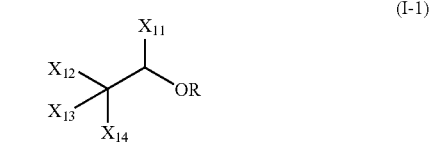

(I-1)

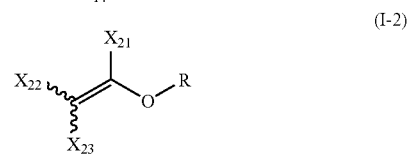

(I-2)

wherein R is a straight-chain, branched-chain or cyclic alkyl group that may have a substituent and/or an unsaturated bond; $X_{11}$ is a halogen atom other than a fluorine atom; $X_{12}$, $X_{13}$, and $X_{14}$ each independently are a halogen atom; $X_{21}$ is a halogen atom other than a fluorine atom; and $X_{22}$ and $X_{23}$ each independently are a halogen atom.

17 Claims, No Drawings

METHOD OF PRODUCING A FLUORINE-CONTAINING VINYL ETHER COMPOUND

FIELD OF THE INVENTION

The present invention relates to a method of producing a fluorine-containing vinyl ether compound, in particular a perfluorovinyl ether compound, that is useful as a raw material for fluorine-containing resins; to a method of producing a fluorine-containing ω-vinyloxy-1-alkene compound, in particular a perfluoro(ω-vinyloxy-1-alkene); and to a novel chloroperfluoro(4-vinyloxy-1-butene), and a method of producing the same.

BACKGROUND OF THE INVENTION

Fluorine-containing vinyl ether compounds, in particular perfluorovinyl ether compounds, are industrially important monomers, because they can give resins that are excellent in physical and chemical properties, such as chemical resistance, heat resistance, low refractive index, and low intermolecular interaction, and also in heat processability, by copolymerization with tetrafluoroethylene.

A known method of synthesizing a perfluorovinyl ether compound is to thermally decompose a perfluoro(2-alkoxypropionic acid) derivative, obtained by reaction of a perfluorocarboxylic acid fluoride (perfluoro acyl fluoride) with hexafluoropropylene oxide (HFPO) (formula 1) (see, for example, U.S. Pat. Nos. 3,291,843, 3,321,532, and 3,351,619).

Patent Nos. 201,871 and 269,933); a method of chlorinating, fluorinating, and dechlorinating, in this order, a vinyl ether obtained in reaction of a perfluoroalkyl methoxide with tetrafluoroethylene (formula 3) (see, for example, U.S. Pat. No. 5,350,497, and Journal of Organic Chemistry, Vol. 59 (1994) 4332–4335).

Formula 2

Formula 3

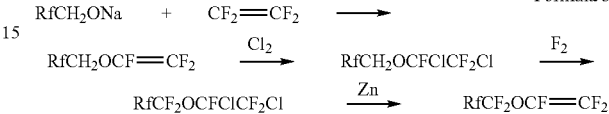

However, it is not feasible industrially to use the method of formula 2, because the reaction of a perfluoroalkyl hypofluoride with 1,2-dichlorodifluoroethylene should be performed at an extremely low temperature. Further, the method of formula 3 has such problems that the reaction proceeds in multiple reaction steps; tetrafluoroethylene used in the reaction is a substance whose transport is prohibited and that should be produced at the same production site; and chlorine gas, which is difficult to handle, should be used. Further, in the methods of formula 1, 2 or 3, there is limitation on the structure of the perfluorovinyl ether pos- Formula 1

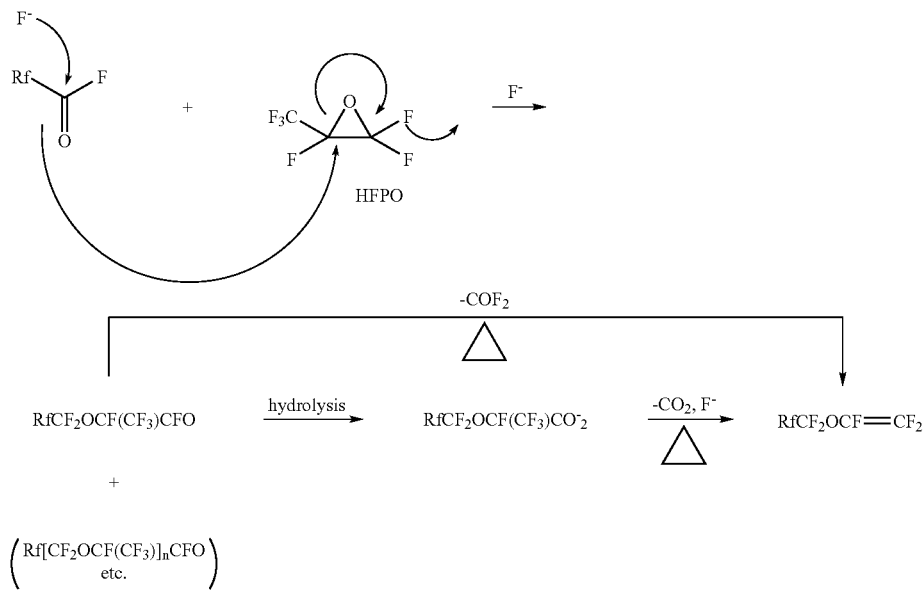

However, it is difficult to produce the desired perfluoro (2-alkoxypropionic acid) derivative in good yield, because of side reactions, such as oligomerization, in the reaction of a perfluorocarboxylic acid fluoride and HFPO. Known means to overcome the problem include, for example, a method of dechlorinating a perfluorodichloroether obtained in reaction of a perfluoroalkyl hypofluoride with 1,2-dichlorodifluoroethylene (formula 2) (see, for example, European sibly produced, because of restriction on the availability of fluorocompounds that are raw materials.

Disclosed as means to overcome these problems are a method of chlorinating, fluorinating, and dechlorinating a desired vinyl ether once prepared (formula 4) (see, for example, Journal of Fluorine Chemistry, 112 (2001) 109–116); and a method of fluorinating and thermally decomposing a desired 2-alkoxypropionic acid derivative once prepared (formulae 5 and 6) (e.g. Journal of Fluorine Chemistry, 112 (2001) 109–116, and International Patent Publication WO 02/20445 pamphlet); and, it became possible to synthesize perfluorovinyl ethers in various structures by these methods.

substance designated as a Class-II specified chemical substance under the Law Concerning Examination and Regulation of Manufacture and Handling of Chemical Substances, and there is danger of explosion under the basic condition.

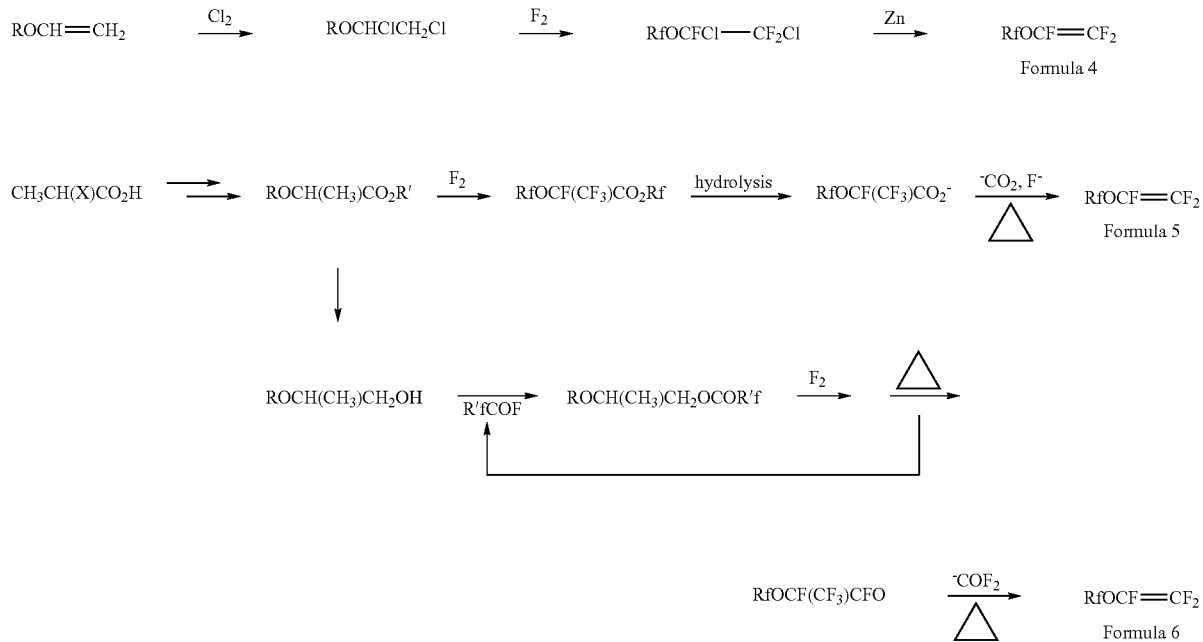

In the above formulae, X represents a halogen atom.

However, the method of formula 4 has the problem that it is not so easy to synthesize the vinyl ether. That is, a vinyl ether can be prepared, for example, by (1) reaction of an alcohol with acetylene, (2) thermal decomposition of an acetaldehyde dialkyl acetal, or (3) de-hydrohalogenation of a 2-halo-1-alkoxyethane; but, these methods also have problems, for example, that it is necessary to use acetylene, a hazardous explosive substance, in the method (1); a high temperature of 300° C. or higher is needed, and the yield is not always good, in the method (2); and, it is difficult to prepare a 2-halo-1-alkoxyethane in good yield, in the method (3). Further, the method of formula 4 also has problems; for example, that dichloroether after chlorination is unstable, and the fluorination yield is not always high. Further, the methods of formula 5 or 6 have a problem in requiring a multi-step process for preparation of a perhalovinyl ether from the starting material 2-halopropionic acid.

As shown in the following formula 7, JP-T-2003–508374 ("JP-T" means searched and published International patent application) describes a synthetic route for preparing an acyl fluoride having a vic-dichloro structure, for use as a precursor of perfluorovinyl ether, by preparing a 1,2-dichlorovinyl ether in reaction of trichloroethylene with an alcohol under a basic condition, and then fluorinating it. However, the synthetic route is not favorable as an industrial-scale method, because the starting material necessary in the synthetic route: trichloroethylene, is an environmental pollution

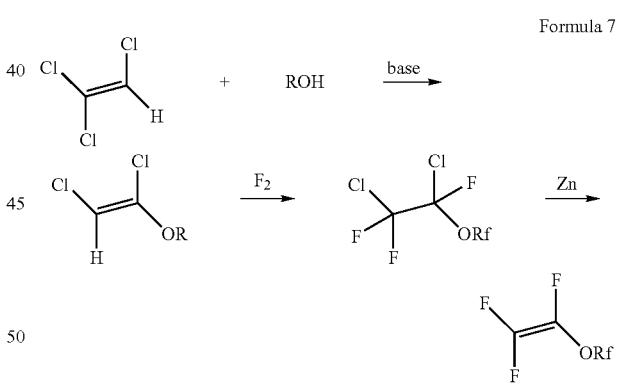

As described above, although there are currently many known methods of synthesizing perfluorovinyl ethers, they carry problems of their own, and there is a strong demand for development of a method to produce perfluorovinyl ether compounds applicable to synthesis of compounds in a variety of structures easily from readily available environment-friendly raw materials.

On the other hand, perfluoro(ω-vinyloxy-1-alkenes), such as perfluoro(4-vinyloxy-1-butene), are known to give amorphous perfluororesins by cyclization-polymerization by a radical initiator (e.g. Nippon Kagakukaishi JP by the Chemical Society of Japan, 2001, No. 12, 659–667). These perfluororesins, which have the characteristics of conventional tetrafluoroethylene-derived fluoropolymers, i.e. properties, such as high heat resistance, high chemical resistance, low refractive index, and low dielectric constant, as well as solubility in solvents and transparency in a wide wavelength range, including ultraviolet, visible, and near-infrared ranges, are useful as high-performance optical materials for pellicle, optical fiber, antireflective film, and the like.

It is possible to synthesize perfluoro(ω-vinyloxy-1-alkenes) by combined use of fluorine-containing fundamental materials, for example, according to the synthetic route to perfluoro(4-vinyloxy-1-butene) (formula 8) described in JP-A-1-143843 ("JP-A" means unexamined published Japanese patent application), the synthetic route to perfluoro(4-vinyloxy-1-butene) (formula 9) described in JP-A-2-311436, or the synthetic route to perfluoro(4-vinyloxy-1-propene) (formula 10) described in JP-A-54-163507, as shown below. However, these methods also had the problems that the raw materials were expensive, the handling efficiency was poor, and the degree of freedom in designing a target molecule was quite low.

As means to solve the above-mentioned problems, JP-A-2001-240576 and JP-A-2005-68044 disclose the methods of using liquid-phase direct fluorination reactions of formula 11 or formula 12, respectively. It became possible to synthesize perfluoro(ω-vinyloxy-1-alkenes) having desirable skeleton by these methods. However, the method of formula 11 has a greater number of steps and is not an efficient and economical method. On the other hand, the method of formula 12 has drastically simplified steps, but it still demands use of a transport-prohibited substance: tetrafluoroethylene.

In the above formulae 1 to 7 and the following formulae 11 and 12, Rf represents a fluorine-containing alkyl group.

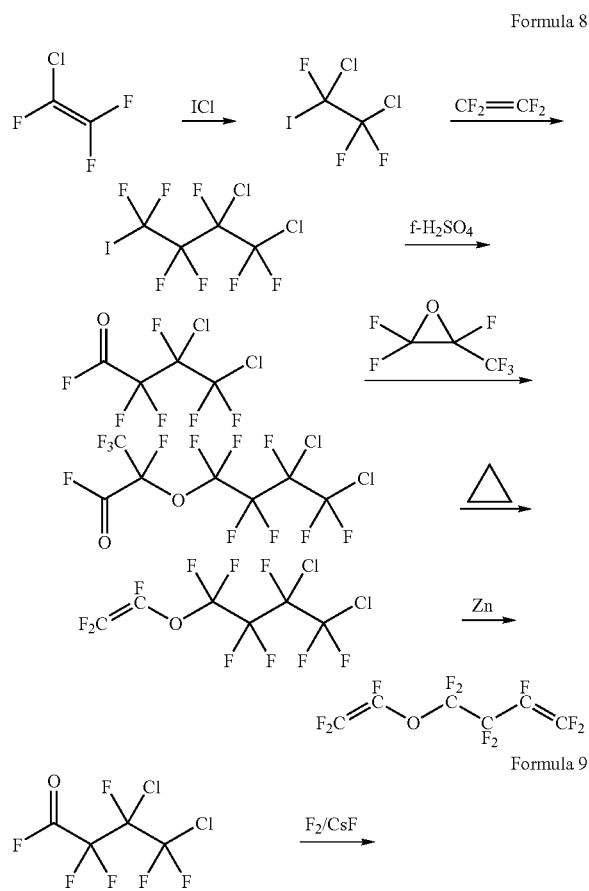

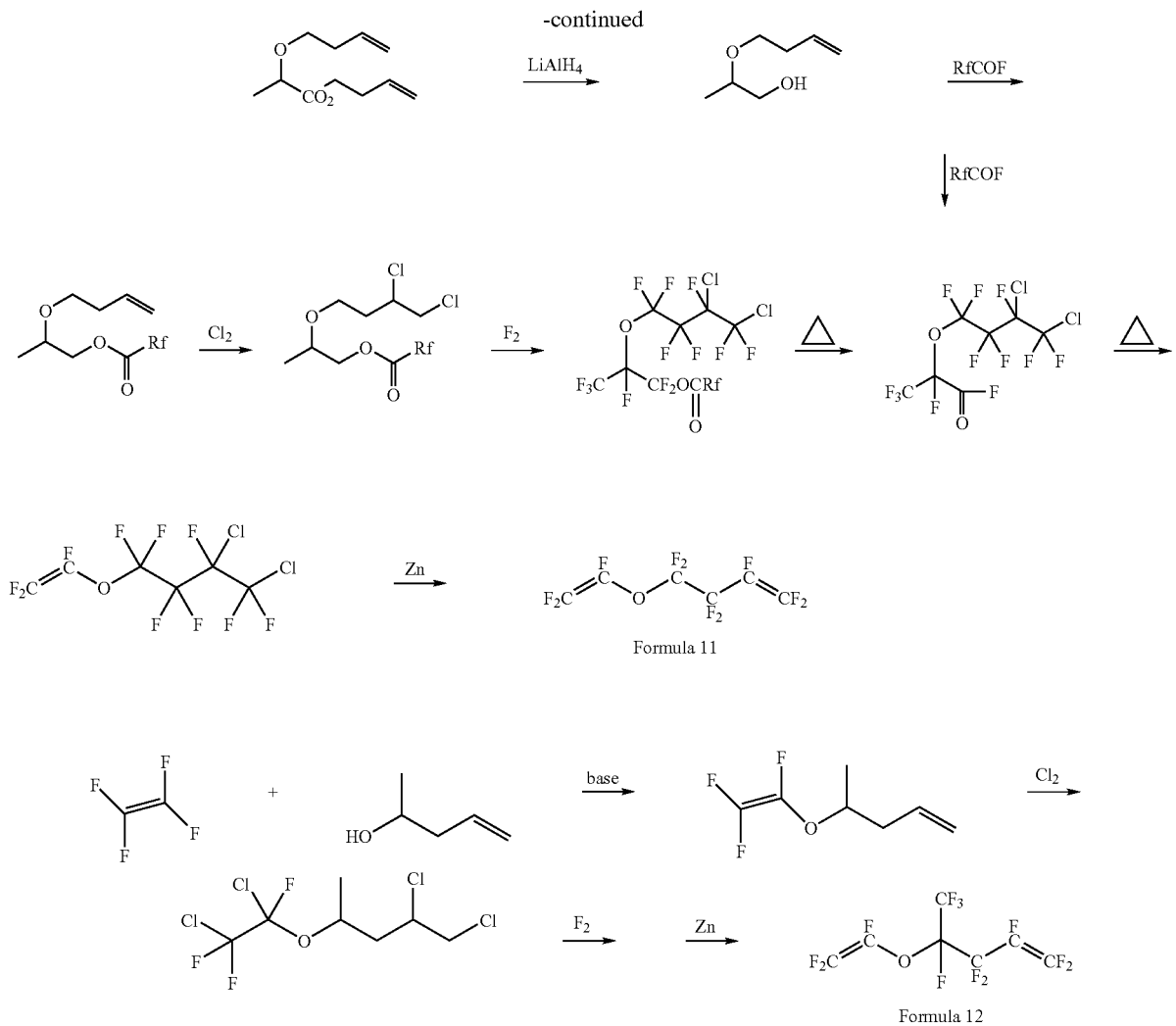

SUMMARY OF THE INVENTION

The present invention resides in a method of producing a fluorine-containing vinyl ether compound, comprises the step of:

fluorinating a compound represented by the following formula (I-1) or (I-2):

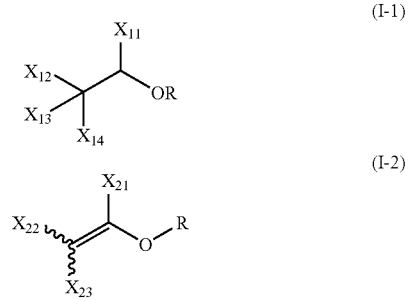

wherein R represents a straight-chain, branched-chain or cyclic alkyl group that may have a substituent and/or an unsaturated bond; $X_{11}$ represents a halogen atom other than a fluorine atom; $X_{12}$, $X_{13}$, and $X_{14}$ each independently represent a halogen atom; $X_{21}$ represents a halogen atom other than a fluorine atom; and $X_{22}$ and $X_{23}$ each independently represent a halogen atom.

Further, the present invention resides in a compound of $CClF=CFOCF_2CF_2CF=CF_2$.

Further, the present invention resides in a compound of $CCl_2=CFOCF_2CF_2CF=CF_2$.

Further, the present invention resides in a compound of $CF_2=CFOCF(CF_2CF_3)CF_2CF=CF_2$.

Other and further features and advantages of the invention will appear more fully from the following description.

DETAILED DESCRIPTION OF THE INVENTION

According to the present invention, there is provided the following means:

(1) A method of producing a fluorine-containing vinyl ether compound, comprising the step of:

fluorinating a compound represented by formula (I-1) or (I-2):

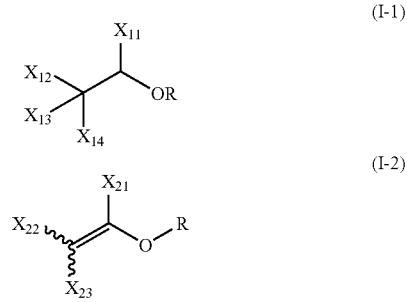

wherein R represents a straight-chain, branched-chain or cyclic alkyl group that may have a substituent and/or an unsaturated bond; $X_{11}$, represents a halogen atom other than a fluorine atom; $X_{12}$, $X_{13}$, and $X_{14}$ each independently represent a halogen atom; $X_{21}$ represents a halogen atom other than a fluorine atom; and $X_{22}$ and $X_{23}$ each independently represent a halogen atom.

(2) The method of producing a fluorine-containing vinyl ether compound according to (1), wherein perfluorinating is conducted, in the fluorinating step.

(3) The method of producing a fluorine-containing vinyl ether compound according to (1) or (2), which comprises the step of: dehalogenating a resultant fluorinated compound, after the fluorinating step.

(4) The method of producing a fluorine-containing vinyl ether compound according to any one of (1) to (3), wherein each of $X_{11}$ and $X_{12}$ in the compound represented by formula (I-1) or (I-2) is a chlorine atom.

(5) The method of producing a fluorine-containing vinyl ether compound according to any one of (1) to (4), which comprises the steps of: fluorinating the compound represented by formula (I-1), to give a compound represented by formula (II-1); and dehalogenating a compound represented by formula (II'-1), to give a compound represented by formula (III-1):

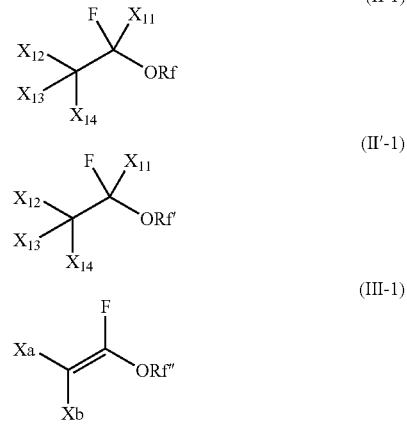

wherein, in formula (II-1), Rf represents a fluorine-containing alkyl group, in which at least one C—H bond in R in formula (I-1) is converted to a C—F bond; $X_{11}$, represents a halogen atom other than a fluorine atom; and $X_{12}$, $X_{13}$, and $X_{14}$ each independently represent a halogen atom; wherein, in formula (II'-1), Rf' has the same meaning as Rf in formula (II-1), or represents a group obtained by modification of a functional group of said Rf; $X_{11}$, represents a halogen atom other than a fluorine atom; and $X_{12}$, $X_{13}$, and $X_{14}$ each independently represent a halogen atom; and wherein, in formula (III-1), Rf" has the same meaning as Rf' in formula (II'-1), or represents a group obtained by modification of said Rf in the dehalogenation step; and Xa and Xb each represent a halogen atom derived from $X_{12}$, $X_{13}$ or $X_{14}$ in formula (II'-1).

(6) The method of producing a fluorine-containing vinyl ether compound according to (5), wherein $X_{11}$ represents a chlorine atom in formulae (I-1), (II-1) and (II'-1).

(7) The method of producing a fluorine-containing vinyl ether compound according to (5) or (6), wherein any one of $X_{12}$, $X_{13}$, and $X_{14}$ is a chlorine atom, and the remaining two each are a fluorine atom in formulae (I-1), (II-1) and (II'-1); and Xa and Xb each are a fluorine atom in formula (III-1).

(8) The method of producing a fluorine-containing vinyl ether compound according to (5) or (6), wherein any two of $X_{12}$, $X_{13}$, and $X_{14}$ each are a chlorine atom, and the remaining one is a fluorine atom in formulae (I-1), (II-1) and (II'-1); and one of Xa and Xb is a chlorine atom, and the other is a fluorine atom in formula (III-1).

(9) The method of producing a fluorine-containing vinyl ether compound according to (5) or (6), wherein $X_{12}$, $X_{13}$, and $X_{14}$ each are a fluorine atom in formulae (I-1), (II-1) and (II'-1), and Xa and Xb each are a fluorine atom in formula (III-1).

(10) The method of producing a fluorine-containing vinyl ether compound according to (5) or (6), wherein $X_{12}$, $X_{13}$, and $X_{14}$ each are a chlorine atom in formulae (I-1), (II-1) and (II'-1), and Xa and Xb each are a chlorine atom in formula (III-1)

(11) The method of producing a fluorine-containing vinyl ether compound according to any one of (1) to (10), wherein the compound represented by formula (I-1) is obtained by chlorination of a compound represented by formula (IV-1):

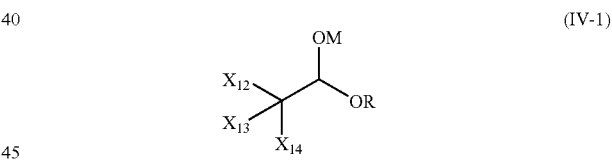

wherein R represents a straight-chain, branched-chain or cyclic alkyl group that may have a substituent and/or an unsaturated bond; $X_{12}$, $X_{13}$, and $X_{14}$ each independently represent a halogen atom; and M represents a hydrogen atom, ammonium, or a metal.

(12) The method of producing a fluorine-containing vinyl ether compound according to any one of (1) to (4), which comprises the steps of: fluorinating the compound represented by formula (I-2), to give a compound represented by formula (II-2); and dehalogenating a compound represented by formula (II'-2), to give a compound represented by formula (III-2):

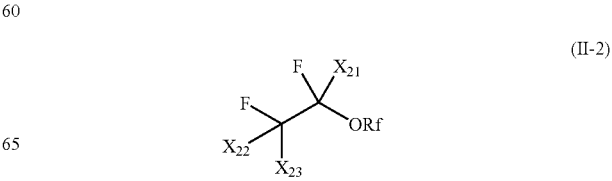

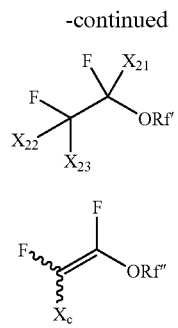

wherein, in formula (II-2), Rf represents a fluorine-containing alkyl group, in which at least one C—H bond of R in formula (I-2) is converted to a C—F bond; $X_{21}$ represents a halogen atom other than a fluorine atom; and $X_{22}$ and $X_{23}$ each independently represent a halogen atom; wherein, in formula (II'-2), $X_{12}$ represents a halogen atom other than a fluorine atom; $X_{22}$ and $X_{23}$ each independently represent a halogen atom; and Rf' has the same meaning as Rf in formula (II-2), or represents a group obtained by modification of a functional group of Rf; and wherein, in formula (III-2), Xc represents a halogen atom derived from $X_{22}$ or $X_{23}$, Rf" has the same meaning as Rf' in formula (II'-2), or represents a group obtained by modification of the Rf' in the dehalogenation step.

(13) The method of producing a fluorine-containing vinyl ether compound according to (12), wherein $X_{21}$ and $X_{22}$ each are a chlorine atom.

(14) The method of producing a fluorine-containing vinyl ether compound according to (12) or (13), wherein $X_{23}$ is a fluorine atom.

(15) The method of producing a fluorine-containing vinyl ether compound according to (12) or (13), wherein $X_{23}$ is a chlorine atom.

(16) The method of producing a fluorine-containing vinyl ether compound according to any one of (1) to (15), wherein R in the compound represented by formula (I-1) or formula (I-2) is a group represented by -L-CHClCH$_2$Cl, in which L represents a straight-chain, branched-chain or cyclic alkylene chain that may have a substituent and/or an unsaturated bond.

(17) A method of producing a compound represented by formula (III), comprising the step of;

fluorinating a compound represented by formula (1), to give a compound represented by formula (II); and dehalogenating the compound represented by formula (II):

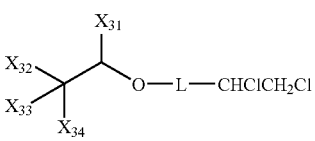

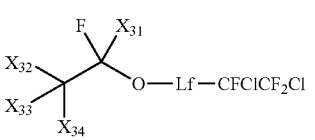

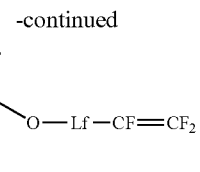

wherein, in formula (1), L represents a straight-chain, branched-chain or cyclic alkylene chain that may contain a substituent and/or an unsaturated bond; $X_{31}$ represents a halogen atom other than a fluorine atom; and $X_{32}$, $X_{33}$, and $X_{34}$ each independently represent a halogen atom; wherein, in formula (II), Lf represents a fluorine-containing alkylene chain obtained by converting at least one C—H bond of L in formula (I) to a C—F bond; and $X_{31}$, $X_{32}$, $X_{33}$, and $X_{34}$ have the same meanings, respectively, as $X_{31}$, $X_{32}$, $X_{33}$, and $X_{34}$ in formula (1); and wherein, in formula (III), Lf has the same meaning as Lf in formula (II); and Xa and Xb each represent a halogen atom derived from $X_{32}$, $X_{33}$ or $X_{34}$.

(18) A method of producing a compound represented by formula (VI), comprising the step of;

fluorinating a compound represented by formula (IV), to give a compound represented by formula (V); and dehalogenating the compound represented by formula (V):

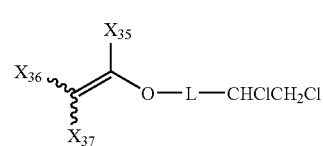

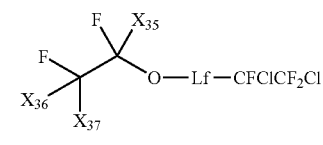

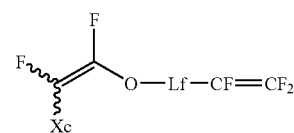

wherein, in formula (IV), L represents a straight-chain, branched-chain or cyclic alkylene chain that may contain a substituent and/or an unsaturated bond; $X_{35}$ represents a halogen atom other than a fluorine atom; and $X_{36}$ and $X_{37}$ each independently represent a halogen atom; wherein, in formula (V), Lf represents a fluorine-containing alkylene chain obtained by modification of at least one C—H bond of L in formula (IV) to a C—F bond; and $X_{35}$, $X_{36}$, and $X_{37}$ have the same meanings, respectively, as $X_{35}$, $X_{36}$, and $X_{37}$ in formula (IV); and wherein, in formula (VI), Lf has the same meaning as Lf in formula (V); and Xc represents a halogen atom derived from $X_{36}$ or $X_{37}$.

(19) The method of producing a compound represented by formula (III) according to (17), wherein Lf is a perfluoroalkylene chain obtained by converting all C—H bonds in the alkylene chain represented by L to C—F bonds.

(20) The method of producing a compound represented by formula (VI) according to (18), wherein Lf is a perfluoroalkylene chain obtained by converting all C—H bonds in the alkylene chain represented by L to C—F bonds.

(21) The method of producing a compound represented by formula (III) according to (17) or (19), wherein $X_{31}$ is a chlorine atom in formulae (I) and (II).

(22) The method of producing a compound represented by formula (III) according to (17), (19) or (21), wherein any one of $X_{32}$, $X_{33}$ and $X_{34}$ is a chlorine atom, and the remaining two each are a fluorine atom in formulae (I) and (II); and Xa and Xb each are a fluorine atom in formula (III).

(23) The method of producing a compound represented by formula (III) according to (17), (19) or (21), wherein any two of $X_{32}$, $X_{33}$, and $X_{34}$ each are a chlorine atom, and the remaining one is a fluorine atom in formulae (1) and (II); and one of Xa and Xb is a chlorine atom and the other is a fluorine atom in formula (III).

(24) The method of producing a compound represented by formula (III) according to (17), (19) or (21), wherein $X_{32}$, $X_{33}$, and $X_{34}$ each are a fluorine atom in formulae (I) and (II), and Xa and Xb each are a fluorine atom in formula (III).

(25) The method of producing a compound represented by formula (III) according to (17), (19) or (21), wherein $X_{32}$, $X_{33}$, and $X_{34}$ each are a chlorine atom in formulae (I) and (II), and Xa and Xb each are a chlorine atom in formula (III).

(26) The method of producing a compound represented by formula (VI) according to (18) or (20), wherein $X_{35}$ and $X_{36}$ each are a chlorine atom.

(27) The method of producing a compound represented by formula (VI) according to (18), (20) or (26), wherein $X_{37}$ is a fluorine atom.

(28) The method of producing a compound represented by formula (VI) according to (18), (20) or (26), wherein $X_{37}$ is a chlorine atom.

(29) The method of producing a compound represented by formula (III) according to (17), (19), (21), (22), (23), (24) or (25), wherein L is $CH_2$, and Lf if $CF_2$.

(30) The method of producing a compound represented by formula (VI) according to (18), (20), (26), (27) or (28), wherein L is $CH_2$, and Lf is $CF_2$.

(33) The method of producing a compound represented by formula (III) according to (17), (19), (21), (22), (23), (24) or (25), wherein L is $CH_2CH_2$, and Lf is $CF_2CF_2$.

(34) The method of producing a compound represented by formula (VI) according to (18), (20), (26), (27) or (28), wherein L is $CH_2CH_2$, and Lf is $CF_2CF_2$.

(35) The method of producing a compound represented by formula (III) according to (17), (19), (21), (22), (23), (24) or (25), wherein L is $CH_2CH_2CH_2$, and Lf is $CF_2CF_2CF_2$.

(36) The method of producing a compound represented by formula (VI) according to (18), (20), (26), (27) or (28), wherein L is $CH_2CH_2CH_2$, and Lf is $CF_2CF_2CF_2$.

(37) A compound represented by $CClF=CFOCF_2CF_2CF=CF_2$.

(38) A compound represented by $CCl_2=CFOCF_2CF_2CF=CF_2$.

(39) A compound represented by $CF_2=CFOCF(CF_2CF_3)CF_2CF=CF_2$.

The best mode for carrying out the present invention is described in detail below.

First, the method of producing a fluorine-containing vinyl ether compound according to the present invention will be described in detail.

The method of producing a fluorine-containing vinyl ether compound according to the present invention comprises the step of: fluorinating a compound represented by formula (I-1) or (I-2) that is used as a starting material. In the present invention, the term "fluorinating (or fluorination)" means to substitute an atom (e.g., hydrogen atom) with a fluorine atom, and/or to add fluorine atoms to a carbon-carbon unsaturated bond.

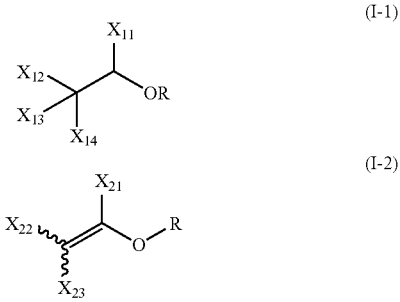

Various methods of converting (most or all of) C—H bonds in a compound to C—F bonds are known, and examples thereof include a method of using cobalt trifluoride, a method of conducting fluorination reaction, by using, as a fluorine source, hydrogen fluoride generated in electrolysis in an electrolytic bath (hereinafter, referred to as electrolytic fluorination), and a method of conducting fluorination directly in a liquid phase, by using a fluorine gas (hereinafter, referred to as liquid-phase direct fluorination). In the present invention, any one of these reactions may be used for fluorination. However, the method of using cobalt trifluoride and the method of using fluorination reaction by electrolytic fluorination may cause the problems of isomerization, cleavage of main chain, and/or recombination reaction, and thus to make it difficult to obtain the desired compound at high purity. Accordingly, use of liquid-phase direct fluorination reaction is more preferable for the fluorination of a compound in the present invention In the present invention, the fluorination is preferably perfluorination. Herein, the term "perfluorination (or perfluorinating)" means to convert all C—H bonds in a compound to C—F bonds, and/or to add $F_2$ to carbon-carbon unsaturated bonds, if present, completely, to make all the carbon-carbon unsaturated bonds be saturated by fluorine atoms.

In the present invention, the liquid-phase direct fluorination reaction is preferably performed in a similar manner to the method described in U.S. Pat. No. 5,093,432, i.e., by a method of supplying a compound represented by formula (I-1) or (I-2) and a theoretical amount or more of fluorine gas diluted with an inert gas, e.g. nitrogen or helium, simultaneously, into a solvent saturated with fluorine. The compound represented by formula (I-1) or (I-2) may be added, after it had been diluted in a solvent, or as it is without dilution.

In the present invention, a solvent preferable for use in the liquid-phase direct fluorination reaction is a solvent that does not react with the fluorine gas under the reaction condition, i.e.; a solvent containing no C—H bond and no carbon-carbon unsaturated bond; and preferable examples thereof include perfluoroalkanes, and perfluorinated compounds having one or more atoms selected from chlorine atom, nitrogen atom and oxygen atom in the structure.

Examples of the solvents include perfluoroalkane compounds (e.g. FC-72 (trade name, manufactured by Sumitomo 3M Limited)), perfluoroether compounds (e.g. FC-75, FC-77 (trade names, manufactured by Sumitomo 3M Limited)), perfluoropolyether compounds (e.g. Krytoxg (trademark, manufactured by Du Pont Kabushiki Kaisha), Fomblin® (trademark, manufactured by Ausimont), Galden®

(trademark, manufactured by Ausimont), Demnam (trade name, manufactured by Daikin Industries, Ltd.)), chlorofluorocarbons (e.g. CFC-11, CFC-113), chlorofluoropolyether compounds, perfluorotrialkylamine compounds, inactive fluids (Fluorinert®, trademark, manufactured by 3M).

In the reaction mentioned in the above, the reaction temperature is preferably −78° C. to 100° C., more preferably −50° C. to 80° C., and further preferably −20° C. to 50° C. The reaction pressure is preferably atmospheric pressure to 2 MPa, and more preferably atmospheric pressure.

When the fluorination does not reach perfluorination after supply of the compound represented by formula (I-1) or (I-2), it is possible to complete the perfluorination reaction in a shorter period of time, if necessary, by supplying a C—H bond- and/or an unsaturated bond-containing compound other than the compound represented by formula (I-1) or (I-2) together with the fluorine gas, or by irradiation the reaction system with a ultraviolet ray while supplying the fluorine gas. Preferable examples of the C—H bond- and/or unsaturated bond-containing compounds include benzene, toluene, and hexafluorobenzene. The amount of the C—H bond- and/or unsaturated bond-containing compound to be added is preferably 0.1 to 10 mol %, more preferably 0.1 to 5 mol %, to the hydrogen atoms in the compound represented by formula (I-1) or (I-2).

Hydrogen fluoride is generated as a byproduct along the progress of the fluorination reaction, and thus, for removal of the hydrogen fluoride it is preferable to add a fluoride hydrogen scavenger to the reaction system or bring the discharge gas into contact with a hydrogen fluoride scavenger at the reactor gas outlet. Examples of the hydrogen fluoride scavengers include organic bases, e.g., trialkylamines, and alkali metal fluorides, e.g., NaF and KF; and the hydrogen fluoride scavenger is more preferably NaF.

When a fluoride hydrogen scavenger is to coexist in the reaction system, the amount of the fluoride hydrogen scavenger to be added is preferably 1 to 20 times, more preferably 1 to 5 times the total amount of the hydrogen atoms present in the compound represented by formula (I-1) or (I-2).

In the present invention, the dehalogenation step may be conducted by any one of known methods using a metal or a metal-containing reducing agent (e.g., those described in U.S. Pat. Nos. 4,533,741 and 4,908,461, JP-A-11-335309, and by M. Hudlicky, "Chemistry of Organofluorine Compounds", Norwood, N.Y., 483–484 (1992)). A fluorine-containing vinyl ether compound can be formed in this step.

Preferable examples of the metals include zinc, magnesium, copper, and the like. Further, preferable examples of the metal-containing reducing agents include $TiCl_4/LiAlH_4$. Generally, the reaction condition for removing neighboring two chlorine atoms at the same time is milder than that for removing neighboring fluorine and chlorine atoms one by one.

Examples of the solvents preferable for reduction by using a metal, e.g. zinc, magnesium, or copper, include amide-series solvents, e.g., N,N-dimethylformamide, N,N-dimethylacetamide, and N-methylpyrrolidone; ether-series solvents, e.g., dioxane, tetrahydrofuran, ether, diglyme, and tetraglyme; alcohol-series solvents, e.g., methanol, ethanol, isopropanol, and butanol. An organic carboxylic acid, e.g., formic acid, acetic acid, or propionic acid, or a halogen molecule, e.g., bromine or iodine, may be added for acceleration of the reaction. The reaction temperature depends on the metal to be used, but is preferably 40 to 160° C. and more preferably 60 to 120° C.

The solvent preferable when $TiCl_4/LiAlH_4$ is used is an ether-series solvent, e.g., dioxane, tetrahydrofuran, ether, diglyme, or tetraglyme, and the reaction temperature is preferably −10 to 50° C. and more preferably 5 to 25° C.

Next, a preferable embodiment of the present invention using the compound represented by formula (I-1) will be described.

In formula (I-1), R represents a straight-chain, branched-chain or cyclic alkyl group that may contain a substituent and/or an unsaturated bond, preferably a substituted or unsubstituted alkyl group having 1 to 30 carbon atoms, more preferably having 1 to 20 carbon atoms, that may contain an unsaturated bond, e.g., carbon-carbon double bond or carbon-carbon triple bond, in the alkyl chain; and examples thereof include methyl, ethyl, propyl, butyl, 3-butenyl, 2-ethylhexyl, cyclohexyl, octyl, dodecyl, and methoxyethly. $X_{11}$ represents a halogen atom other than a fluorine atom (e.g., chlorine, bromine, or iodine); and $X_{12}$, $X_{13}$, and $X_{14}$ each independently represent a halogen atom (e.g., fluorine, chlorine, bromine, or iodine). $X_{11}$, is preferably a chlorine atom; and $X_{12}$, $X_{13}$, and $X_{14}$ each are preferably a fluorine or chlorine atom.

Examples of the substituent on R include a halogen atom (e.g., fluorine, chlorine, bromine, and iodine), an alkyl group (preferably a straight-chain, branched-chain or cyclic alkyl group having 1 to 20 carbon atoms, e.g., methyl, ethyl, trifluoromethly, pentafluoroethyl, and heptafluoropropyl), an aryl group (preferably a substituted or unsubstituted aryl group having 6 to 20 carbon atoms, e.g., phenyl, p-tolyl, naphthyl, m-chlorophenyl, and pentafluorophenyl), a cyano group, a hydroxyl group, a nitro group, a carboxyl group, a halocarbonyl group (e.g., chlorocarbonyl, and fluorocarbonyl), an alkoxy group (preferably, a substituted or unsubstituted alkoxy group having 1 to 20 carbon atoms, e.g., methoxy, ethoxy, isopropoxy, t-butoxy, n-octyloxy, 2-methoxyethoxy, trifluoromethoxy, and heptafluoropropoxy), an aryloxy group (preferably, a substituted or unsubstituted aryloxy group having 6 to 20 carbon atoms, e.g., phenoxy, 2-methylphenoxy, 4-trifluoromethlyphenoxy, 3-nitrophenoxy, and pentafluorophenoxy), an acyloxy group (preferably a formyloxy group, a substituted or unsubstituted alkylcarbonyloxy group having 2 to 20 carbon atoms, and a substituted or unsubstituted arylcarbonyloxy group having 6 to 20 carbon atoms, e.g., formyloxy, acetyloxy, trifluoroacetyloxy, heptafluoropropionyloxy, 2,3,3-tetrafluoro-(2-heptafluoropropoxy)propionyloxy, benzoyloxy, and pentafluorobenzoyloxy), a carbamoyloxy group (preferably, a substituted or unsubstituted carbamoyloxy group having 1 to 20 carbon atoms, e.g., N,N-dimethylcarbamoyloxy, N,N-diethylcarbamoyloxy, bis-(2,2,2-trifluoroethyl)carbamoyloxy, and morphorinocarbonyloxy), an alkoxycarbonyloxy group (preferably, a substituted or unsubstituted alkoxycarbonyloxy group having 2 to 20 carbon atoms, e.g., methoxycarbonyloxy, ethoxycarbonyloxy, 2,2,2-trifluoroethoxycarbonyloxy, and n-octyloxycarbonyloxy), an aryloxycarbonyloxy group (preferably, a substituted or unsubstituted aryloxycarbonyloxy group having 7 to 20 carbon atoms, e.g., phenoxycarbonyloxy, and p-pentafluorophenoxycarbonyloxy), an amino group (preferably, a substituted or unsubstituted alkylamino group having 0 to 20 carbon atoms, and a substituted or unsubstituted anilino group having 6 to 20 carbon atoms, e.g., amino, methylamino, dimethylamino, bis-(2,2,2-trifluoroethyl)amino, anilino, and N-trifluoromethlyanilino), an acylamino group (preferably, a substituted or unsubstituted alkylcarbonylamino group having 1 to 20 carbon atoms, and a substituted or unsubstituted arylcarbonylamino group having 6 to 20 carbon atoms, e.g., formylamino, acetylamino, trifluoroacetylamino, and benzoylamino), an aminocarbonylamino group (preferably, a substituted or unsubstituted aminocarbonylamino group having 1 to 20 carbon atoms, e.g., carbamoylamino, N,N-dimethylaminocarbonylamino, N,N-diethylaminocarbonylamino, and morphorinocarbonylamino), an alkoxycarbonylamino group (preferably a substituted or unsubstituted alkoxycarbonylamino group having 2 to 20 carbon atoms, e.g., methoxycarbonylamino, ethoxycarbonylamino, 2,2,2-trifluoroethoxycarbonylamino, and N-trifluoromethly-methoxycarbonylamino), an aryloxycarbonylamino group (preferably a substituted or unsubstituted aryloxycarbonylamino group having 7 to 20 carbon atoms, e.g., phenoxycarbonylamino, and p-chlorophenoxycarbonylamino), a sulfamoylamino group (preferably a substituted or unsubstituted sulfamoylamino group having 0 to 20 carbon atoms, e.g., sulfamoylamino, and N,N-dimethylaminosulfonylamino), an alkyl- or aryl-sulfonylamino group (preferably, a substituted or unsubstituted alkylsulfonylamino group having 1 to 20 carbon atoms, and a substituted or unsubstituted arylsulfonylamino group having 6 to 20 carbon atoms, e.g., methylsulfonylamino, trifluoromethylsulfonylamino, butylsulfonylamino, and phenylsulfonylamino), a mercapto group, an alkylthio group (preferably a substituted or unsubstituted alkylthio group having 1 to 20 carbon atoms, e.g., methylthio, ethylthio, and 2,2,2-trifluoroethylthio), an arylthio group (preferably a substituted or unsubstituted arylthio group having 6 to 20 carbon atoms, e.g., phenylthio, p-chlorophenylthio, and pentafluorophenylthio), a sulfamoyl group (preferably a substituted or unsubstituted sulfamoyl group having 0 to 20 carbon atoms, e.g., N-ethylsulfamoyl, N,N-dimethylsulfamoyl, N,N-bis(2, 2,2-trifluoroethyl)sulfamoyl, N-acetylsulfamoyl, and N-benzoylsulfamoyl), a sulfo group, a halosulfonyl group (e.g., chlorosulfonyl, and fluorosulfonyl), an alkyl- or arylsulfinyl group (preferably, a substituted or unsubstituted alkylsulfinyl group having 1 to 20 carbon atoms, and a substituted or unsubstituted arylsulfinyl group having 6 to 20 carbon atoms, e.g., methylsulfinyl, ethylsulfinyl, and phenylsulfinyl), an alkyl- or aryl-sulfonyl group (preferably, a substituted or unsubstituted alkylsulfonyl group having 1 to 20 carbon atoms, and a substituted or unsubstituted arylsulfonyl group having 6 to 20 carbon atoms, e.g., methylsulfonyl, trifluoromethylsulfonyl, ethylsulfonyl, and phenylsulfonyl), an acyl group (preferably, a substituted or unsubstituted alkylcarbonyl group having 1 to 20 carbon atoms, and a substituted or unsubstituted arylcarbonyl group having 7 to 20 carbon atoms, e.g., acetyl, trifluoroacetyl, pivaloyl, heptafluoropropionyl, benzoyl, and pentafluorobenzoyl), an aryloxycarbonyl group (preferably a substituted or unsubstituted aryloxycarbonyl group having 7 to 20 carbon atoms, e.g., phenoxycarbonyl, and o-chlorophenoxycarbonyl), an alkoxycarbonyl group (preferably a substituted or unsubstituted alkoxycarbonyl group having 2 to 20 carbon atoms, e.g., methoxycarbonyl, ethoxycarbonyl, 2,2,2-trifluoroethoxycarbonyl, 2,2,3,3,4,4-hexafluorobutoxycarbonyl, and 2,2,3,3,4,4,4-heptafluorobutoxycarbonyl), a carbamoyl group (preferably a substituted or unsubstituted carbamoyl group having 1 to 3 carbon atoms, e.g., carbamoyl, N-methylcarbamoyl, N,N-dimethylcarbamoyl, and N,N-bis(2,2,2-trifluoroethyl)carbamoyl), and an imido group (preferably, N-succinimido, and N-phthalimido).

Among these, more preferable examples of the substituent include a fluorine atom, a chlorine atom, an alkyl group, a hydroxyl group, a halocarbonyl group, an alkoxy group, an acyloxy group, an alkoxycarbonyloxy group, a halosulfonyl group, an alkylsulfonyl group, an acyl group, or an alkoxycarbonyl group.

The production method according to the present invention preferably comprises the steps of: fluorinating a compound represented by formula (I-1), to give a compound represented by formula (II-1); and dehalogenating a compound represented by formula (II'-1), to give a compound represented by formula (III-1). In formula (II-1), Rf represents a fluorine-containing alkyl group, i.e., an R-derived group in which at least one C—H bond in R is converted to a C—F bond; and $X_{11}$, $X_{12}$, $X_{13}$, and $X_{14}$ have the same meanings as those described above. Rf preferably represents a perfluoroalkyl group, i.e., an R-derived group in which all C—H bonds in R are converted to C—F bonds (and $F_2$ is added to the double bond(s) in R, if present, to saturate each double bond). In formula (II'-1), Rf' has the same meaning as Rf, or it represents a group of Rf that is obtained by modification of any functional group(s) therein; and $X_{11}$, $X_{12}$, $X_{13}$, and $X_{14}$ have the same meanings as those described above. Herein, the term "modification of any functional group(s)" means a reaction to convert a group that is a substituent on the alkyl chain to another group (e.g., thermal decomposition or hydrolysis of an ester group), and it is not particularly limited, and it may be a combination of plural conversion reactions. In formula (III-1), Rf" has the same meaning as Rf', or represents a group obtained by modification in the dehalogenation step; and Xa and Xb each represent a halogen atom derived from $X)_2$, $X_{13}$ or $X_{14}$.

In the present invention, the compound represented by formula (I-1) is preferably a compound obtained by chlorination of the compound represented by formula (IV-1). In formula (IV-1), $X_{12}$, $X_{13}$, $X_{14}$, and R have the same meanings as those described above; and M represents a hydrogen atom, an ammonium (e.g., tetramethylammonium, tetraethylammonium, tetrapropylammonium, tetrabutylammonium, or tributylmethylammonium), or a metal (sodium, potassium, magnesium, zinc, aluminum, copper, or silver; said metal can have any valency or may have a bonding to a chemical species other than the compound of formula (IV-1)), and is preferably a hydrogen atom.

The step of fluorinating the compound represented by formula (I-1) may contains a step of fluorinating the compound represented by formula (I-1), to give a compound represented by formula (II-1), preferably a step of perfluorinating the compound represented by formula (I-1).

The amount of fluorine to be supplied for fluorination of the compound represented by formula (I-1) is preferably 0.9 to 5.0 equivalences, more preferably 1.1 to 2.0 equivalences, to the hydrogen atoms in the compound (I-1) to be substituted with fluorine.

Next, the method of converting the compound represented by formula (IV-1) to the compound represented by formula (I-1) will be described. Any one of common chlorinating agents used for chlorination of alcohols may be used in this step. Preferable examples of the chlorinating agents include hydrogen chloride, phosphorus trichloride, phosphorus pentachloride, phosphorus oxychloride, thionyl chloride, sulfuryl chloride, $R_3P/CX_4$ (in which R represents an alkyl group, an aryl group, an alkoxy group, or an aryloxy group; and X represents a halogen atom), $R_3PCl_2$ (in which R represents an alkyl group, an aryl group, an alkoxy group, or an aryloxy group), RCOCl (in which R represents an alkyl group or an aryl group), oxalyl chloride, $RSO_2X$ (in which R represents an alkyl group or an aryl group; and X represents a halogen atom), and cyanuric chloride. The chlorinating agent may be used in combination with a metal salt, e.g. LiCl, NaCl, KCl, MgCl$_2$, CaCl$_2$, ZnCl$_2$, or CuCl$_2$. More preferable examples of the chlorinating agents include phosphorus trichloride, phosphorus pentachloride, phosphorus oxychloride, thionyl chloride, and trialkylphosphine/carbon tetrachloride; and it is further preferably thionyl chloride.

The amount of the chlorinating agent to be used is preferably 0.5 to 5 equivalences, more preferably 0.8 to 3 equivalences, and still more preferably 0.9 to 1.5 equivalences, to the compound represented by formula (IV-1). Further, the reaction may be performed in the presence of an acid or a base. Examples of the acids that can be used include sulfuric acid, hydrochloric acid, bromic acid, sulfonic acid, alkyl- or aryl-sulfonic acids, formic acid, and acetic acid. Examples of the bases that can be used include organic bases, e.g. pyridine, 2-picoline, 4-picoline, 2,6-lutidine, quinoline, triethylamine, N,N-diisopropylethylamine, DBU (1,8-diazabicyclo[5.4.0]undec-7-ene), and DABCO (1,4-diazabicyclo[2.2.2]octane); and inorganic bases, e.g. sodium hydroxide, potassium hydroxide, sodium carbonate, potassium carbonate, sodium bicarbonate, potassium bicarbonate, and sodium acetate. The amount of the base to be added when used is preferably 0.5 to 5 equivalences, more preferably 0.8 to 3 equivalences, and still more preferably 0.9 to 1.5 equivalences, to the compound represented by formula (IV-1).

The reaction may be performed in the absence of any solvent, but a solvent may be used, e.g. dichloromethane, chloroform, carbon tetrachloride, carbon tetrabromide, ethyl acetate, propyl acetate, hexane, tetrahydrofuran, diethyl ether, acetonitrile, toluene, N,N-dimethylformamide, N,N-dimethylacetamide, dimethylsulfoxide, or sulfolane.

The reaction temperature is preferably –30° C. to 150° C., more preferably –10° C. to 100° more preferably 0° C. to 80° C.

The reaction period may vary according to the kinds and amounts to be added of the halogenating agent, any other additive(s), and the solvent, the reaction temperature, and other conditions, but it is preferably 5 minutes to 72 hours, more preferably 30 minutes to 24 hours, and still more preferably 1 to 6 hours, by controlling the conditions mentioned above properly.

The compound represented by formula (IV-1) can be synthesized easily, by an addition reaction of an aldehyde represented by CCl$_n$F$_3$-nCHO with an alcohol represented by ROH (see, for example, U.S. Pat. No. 2,870,219), an alcohol-exchange reaction of a hemiacetal represented by CCl$_n$F$_3$-nC(OH)OR$_1$ (in which R$_1$ represents an alkyl group having 1 to 5 carbon atoms) with an alcohol represented by ROH (see, for example, Journal of Organic Chemistry, Vol. 6 (1941) 831–833), or a reduction reaction of an ester compound represented by CCl$_n$F$_3$-nCO$_2$R (see, for example, Tetrahedron Letters, Vol. 39 (1998) 4071–4074). The compound represented by formula (IV-1) prepared by any of the synthetic methods above may be generated in the reaction system, to subject to the chlorination step as it is, in which isolation or purification of the compound is not always necessary.

Next, a preferable embodiment of the present invention using the compound represented by formula (I-2) will be described.

In formula (I-2), R represents a straight-chain, branched-chain or cyclic alkyl group that may contain a substituent and/or an unsaturated bond, preferably a substituted or unsubstituted alkyl group having 1 to 30 carbon atoms, more preferably 1 to 20 carbon atoms, in which said alkyl group may be any of a straight-chain, a branched-chain or a cyclic form, or may contain a carbon-carbon double bond or a carbon-carbon triple bond in the alkyl chain; and examples thereof include methyl, ethyl, propyl, butyl, 3-butenyl, 2-ethylhexyl, cyclohexyl, octyl, dodecyl, and methoxyethly. $X_{21}$ represents a halogen atom other than a fluorine atom (e.g., chlorine, bromine, or iodine); $X_{22}$ and $X_{23}$ each independently represent a halogen atom (e.g., fluorine, chlorine, bromine, or iodine). $X_2$, and $X_{22}$ each preferably represent a chlorine atom; and $X_{23}$ preferably represents a fluorine or chlorine atom.

Examples of the substituent on R include a halogen atom (e.g., fluorine, chlorine, bromine, or iodine), an alkyl group (preferably a straight-chain, branched-chain or cyclic alkyl group having 1 to 20 carbon atoms, e.g., methyl, ethyl, trifluoromethyl, pentafluoroethyl, and heptafluoropropyl), an aryl group (preferably a substituted or unsubstituted aryl group having 6 to 20 carbon atoms, e.g., phenyl, p-tolyl, naphthyl, m-chlorophenyl, and pentafluorophenyl), a cyano group, a hydroxyl group, a nitro group, a carboxyl group, a halocarbonyl group (e.g., chlorocarbonyl, and fluorocarbonyl), an alkoxy group (preferably a substituted or unsubstituted alkoxy group having 1 to 20 carbon atoms, e.g., methoxy, ethoxy, isopropoxy, t-butoxy, n-octyloxy, 2-methoxyethoxy, trifluoromethoxy, and heptafluoropropoxy), an aryloxy group (preferably a substituted or unsubstituted aryloxy group having 6 to 20 carbon atoms, e.g., phenoxy, 2-methylphenoxy, 4-trifluoromethylphenoxy, 3-nitrophenoxy, and pentafluorophenoxy), an acyloxy group (preferably, a formyloxy group, a substituted or unsubstituted alkylcarbonyloxy group having 2 to 20 carbon atoms, and a substituted or unsubstituted arylcarbonyloxy group having 6 to 20 carbon atoms, e.g., formyloxy, acetyloxy, trifluoroacetyloxy, heptafluoropropionyloxy, 2,3,3-tetrafluoro-(2-heptafluoropropoxy)propionyloxy, benzoyloxy, and pentafluorobenzoyloxy), a carbamoyloxy group (preferably a substituted or unsubstituted carbamoyloxy group having 1 to 20 carbon atoms, e.g., N,N-dimethylcarbamoyloxy, N,N-diethylcarbamoyloxy, bis-(2,2,2-trifluoroethyl)carbamoyloxy, and morphorinocarbonyloxy), an alkoxycarbonyloxy group (preferably a substituted or unsubstituted alkoxycarbonyloxy group having 2 to 20 carbon atoms, e.g., methoxycarbonyloxy, ethoxycarbonyloxy, 2,2,2-trifluoroethoxycarbonyloxy, and n-octyloxycarbonyloxy), an aryloxycarbonyloxy group (preferably a substituted or unsubstituted aryloxycarbonyloxy group having 7 to 20 carbon atoms, e.g., phenoxycarbonyloxy, and p-pentafluorophenoxycarbonyloxy), an amino group (preferably a substituted or unsubstituted alkylamino group having 0 to 20 carbon atoms, and a substituted or unsubstituted anilino group having 6 to 20 carbon atoms, e.g., amino, methylamino, dimethylamino, bis-(2,2,2-trifluoroethyl)amino, anilino, and N-trifluoromethylanilino), an acylamino group (preferably, a substituted or unsubstituted alkylcarbonylamino group having 1 to 20 carbon atoms, and a substituted or unsubstituted arylcarbonylamino group having 6 to 20 carbon atoms, e.g., formylamino, acetylamino, trifluoroacetylamino, and benzoylamino), an aminocarbonylamino group (preferably a substituted or unsubstituted aminocarbonylamino group having 1 to 20 carbon atoms, e.g., carbamoylamino, N,N-dimethylaminocarbonylamino, N,N-diethylaminocarbonylamino, and morphorinocarbonylamino), an alkoxycarbonylamino group (preferably a substituted or unsubstituted alkoxycarbonylamino group having 2 to 20 carbon atoms, e.g., methoxycarbonylamino, ethoxycarbonylamino, 2,2,2-trifluoroethoxycarbonylamino, and N-trifluoromethyl-methoxycarbonylamino), an aryloxycarbonylamino group (preferably a substituted or unsubstituted aryloxycarbonylamino group having 7 to 20 carbon atoms, e.g., phenoxycarbonylamino, and p-chlorophenoxycarbonylamino), a sulfamoylamino group (preferably a substituted or unsubstituted sulfamoylamino group having 0 to 20 carbon atoms, e.g., sulfamoylamino, and N,N-dimethylaminosulfonylamino), an alkyl- or aryl-sulfonylamino group (preferably, a substituted or unsubstituted alkylsulfonylamino group having 1 to 20 carbon atoms, and a substituted or unsubstituted arylsulfonylamino group having 6 to 20 carbon atoms, e.g., methylsulfonylamino, trifluoromethylsulfonylamino, butylsulfonylamino, and phenylsulfonylamino), a mercapto group, an alkylthio group (preferably a substituted or unsubstituted alkylthio group having 1 to 20 carbon atoms, e.g., methylthio, ethylthio, and 2,2,2-trifluoroethylthio), an arylthio group (preferably a substituted or unsubstituted arylthio group having 6 to 20 carbon atoms, e.g., phenylthio, p-chlorophenylthio, and pentafluorophenylthio), a sulfamoyl group (preferably a substituted or unsubstituted sulfamoyl group having 0 to 20 carbon atoms, e.g., N-ethylsulfamoyl, N,N-dimethylsulfamoyl, N,N-bis(2,2,2-trifluoroethyl)sulfamoyl, N-acetylsulfamoyl, and N-benzoylsulfamoyl), a sulfo group, a halosulfonyl group (e.g., chlorosulfonyl, and fluorosulfonyl), an alkyl- or arylsulfinyl group (preferably, a substituted or unsubstituted alkylsulfinyl group having 1 to 20 carbon atoms, and a substituted or unsubstituted arylsulfinyl group having 6 to 20 carbon atoms, e.g., methylsulfinyl, ethylsulfinyl, and phenylsulfinyl), an alkyl- or aryl-sulfonyl group (preferably, a substituted or unsubstituted alkylsulfonyl group having 1 to 20 carbon atoms, and a substituted or unsubstituted arylsulfonyl group having 6 to 20 carbon atoms, e.g. methylsulfonyl, trifluoromethylsulfonyl, ethylsulfonyl, and phenylsulfonyl), an acyl group (preferably, a substituted or unsubstituted alkylcarbonyl group having 1 to 20 carbon atoms, and a substituted or unsubstituted arylcarbonyl group having 7 to 20 carbon atoms, e.g., acetyl, trifluoroacetyl, pivaloyl, heptafluoropropionyl, benzoyl, and pentafluorobenzoyl), an aryloxycarbonyl group (preferably a substituted or unsubstituted aryloxycarbonyl group having 7 to 20 carbon atoms, e.g., phenoxycarbonyl, and o-chlorophenoxycarbonyl), an alkoxycarbonyl group (preferably a substituted or unsubstituted alkoxycarbonyl group having 2 to 20 carbon atoms, e.g., methoxycarbonyl, ethoxycarbonyl, 2,2,2-trifluoroethoxycarbonyl, 2,2,3,3,4,4-hexafluorobutoxycarbonyl, and 2,2,3,3,4,4,4-heptafluorobutoxycarbonyl), a carbamoyl group (preferably a substituted or unsubstituted carbamoyl group having 1 to 30 carbon atoms, e.g., carbamoyl, N-methylcarbamoyl, N,N-dimethylcarbamoyl, and N,N-bis(2,2,2-trifluoroethyl)carbamoyl), and an imido group (preferably, N-succinimido, and N-phthalimido).

Among these, more preferable examples of the substituent include a fluorine atom, a chlorine atom, an alkyl group, a hydroxyl group, a halocarbonyl group, an alkoxy group, an acyloxy group, an alkoxycarbonyloxy group, a halosulfonyl group, a alkylsulfonyl group, an acyl group, or an alkoxycarbonyl group.

In formula (II-2), Rf represents a fluorine-containing alkyl group, i.e., an R-derived group in which at least one C—H bond in R above is converted to a C—F bond; and $X_{21}$, $X_{22}$ and $X_{23}$ have the same meanings as those described above. Rf preferably represents a perfluoroalkyl group, i.e., an R-derived group in which all C—H bonds in R are converted to C—F bonds (and $F_2$ is added to the double bond in R, if any, to saturate each double bond). In formula (II'-2), $X_{21}$, $X_{22}$ and $X_{23}$ have the same meanings as those described above; and Rf' has the same meaning as Rf, or represents a group of Rf that is obtained by modification of any functional group(s). Herein, the term "modification of any functional group(s)" means a reaction to convert a substituent present in the Rf to another group (e.g., thermal decomposition or hydrolysis of an ester group), and is not particularly limited, and may be a combination of plural conversion reactions. In formula (III-2), Xc has the same meaning as that described above; and Rf'' has the same meaning as Rf' above, or represents a group obtained by modification of Rf' in the dehalogenation step.

The step of fluorinating the compound represented by formula (I-2) is a step of giving a compound represented by formula (II-2), and preferably a step of perfluorinating the compound represented by formula (I-2).

The amount of the fluorine to be supplied for fluorination of the compound represented by formula (I-2) is preferably 0.9 to 5.0 equivalences, more preferably 1.1 to 2.0 equivalences, to the hydrogen atoms in the compound (I-2) to be substituted with fluorine.

The raw material in the fluorination step, the compound represented by formula (I-2), can be synthesized easily, for example, according to the method, as shown by formula 13 below, as described in U.S. Pat. No. 2,803,665, and Journal of Organometallic Chemistry, 71, 1974, 335–346.

Formula 13

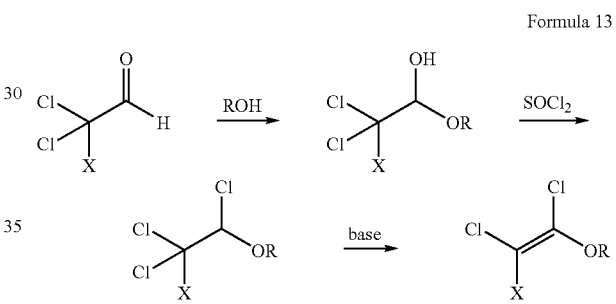

In formula above, X represents a halogen atom.

The dehalogenation step is preferably a step of dehalogenating the compound represented by formula (II'-2), and a fluorine-containing vinyl ether compound represented by formula (III-2) can be formed in this step.

In the present invention, the compound represented by formula (I-1) or (I-2) is preferably a compound represented by formula (I) or (IV); and it is preferable to fluorinate the compound represented by formula (I) or (IV), to give a compound represented by formula (II) or (V), and then dehalogenate the compound represented by formula (II) or (V), to give a fluorine-containing vinyloxy-1-alkene compound represented by formula (III) or (VI).

In formula (1), L represents a straight-chain, branched-chain or cyclic alkylene chain that may contain a substituent and/or an unsaturated bond, preferably a substituted or unsubstituted alkylene chain having 1 to 20 carbon atoms, that may have a carbon-carbon double bond or a carbon-carbon triple bond in the chain. L preferably represents a saturated alkylene chain having 1 to 10 carbon atoms, more preferably 1 to 4 carbon atoms, [e.g., —$CH_2$—, —$CH_2CH_2$—, —$CH_2CH_2CH_2$—, —$CH_2CH_2CH_2CH_2$—, —$CH(CH_3)CH_2$—, —$CH_2CH(CH_3)$—, —$CH_2CH(CH_3)CH_2$—, —$CH(CH_2CH_3)CH_2$—, or —$CH_2CH(CH_2CH_3)$—]; and particularly preferably —$CH_2$— or —$CH_2CH_2$—, $X_{31}$ represents a halogen atom other than a fluorine atom (e.g., chlorine, bromine, or iodine); and $X_{32}$, $X_{33}$, and $X_{34}$ each independently represent a halogen atom (e.g., fluorine, chlorine, bromine, or iodine). $X_3$, is preferably a chlorine atom; and $X_{32}$, $X_{33}$, and $X_{34}$ each preferably represent a fluorine atom or a chlorine atom.

Examples of the substituent on L include a halogen atom (e.g., fluorine, chlorine, bromine, and iodine), an alkyl group (preferably a straight-chain, branched-chain or cyclic alkyl group having 1 to 20 carbon atoms, e.g., methyl, ethyl, trifluoromethyl, pentafluoroethyl, and heptafluoropropyl), an aryl group (preferably a substituted or unsubstituted aryl group having 6 to 20 carbon atoms, e.g., phenyl, p-tolyl, naphthyl, m-chlorophenyl, and pentafluorophenyl), a cyano group, a hydroxyl group, a nitro group, a carboxyl group, a halocarbonyl group (e.g., chlorocarbonyl, and fluorocarbonyl), an alkoxy group (preferably a substituted or unsubstituted alkoxy group having 1 to 20 carbon atoms, e.g., methoxy, ethoxy, isopropoxy, t-butoxy, n-octyloxy, 2-methoxyethoxy, trifluoromethoxy, and heptafluoropropoxy), an aryloxy group (preferably a substituted or unsubstituted aryloxy group having 6 to 20 carbon atoms, e.g., phenoxy, 2-methylphenoxy, 4-trifluoromethylphenoxy, 3-nitrophenoxy, and pentafluorophenoxy), an acyloxy group (preferably, a formyloxy group, a substituted or unsubstituted alkylcarbonyloxy group having 2 to 20 carbon atoms, and a substituted or unsubstituted arylcarbonyloxy group having 6 to 20 carbon atoms, e.g., formyloxy, acetyloxy, trifluoroacetyloxy, heptafluoropropionyloxy, 2,3,3-tetrafluoro-(2-heptafluoropropoxy)propionyloxy, benzoyloxy, and pentafluorobenzoyloxy), a carbamoyloxy group (preferably a substituted or unsubstituted carbamoyloxy group having 1 to 20 carbon atoms, e.g.; N,N-dimethylcarbamoyloxy, N,N-diethylcarbamoyloxy, bis-(2,2,2-trifluoroethyl)carbamoyloxy, and morphorinocarbonyloxy), an alkoxycarbonyloxy group (preferably a substituted or unsubstituted alkoxycarbonyloxy group having 2 to 20 carbon atoms, e.g., methoxycarbonyloxy, ethoxycarbonyloxy, 2,2,2-trifluoroethoxycarbonyloxy, and n-octyloxycarbonyloxy), an aryloxycarbonyloxy group (preferably a substituted or unsubstituted aryloxycarbonyloxy group having 7 to 20 carbon atoms, e.g., phenoxycarbonyloxy, and p-pentafluorophenoxycarbonyloxy), an amino group (preferably, a substituted or unsubstituted alkylamino group having 0 to 20 carbon atoms, and a substituted or unsubstituted anilino group having 6 to 20 carbon atoms, e.g., amino, methylamino, dimethylamino, bis-(2,2,2-trifluoroethyl)amino, anilino, and N-trifluoromethylanilino), an acylamino group (preferably, a substituted or unsubstituted alkylcarbonylamino group having 1 to 20 carbon atoms, and a substituted or unsubstituted arylcarbonylamino group having 6 to 20 carbon atoms, e.g., formylamino, acetylamino, trifluoroacetylamino, and benzoylamino), an aminocarbonylamino group (preferably a substituted or unsubstituted aminocarbonylamino group having 1 to 20 carbon atoms, e.g., carbamoylamino, N,N-dimethylaminocarbonylamino, N,N-diethylaminocarbonylamino, and morphorinocarbonylamino), an alkoxycarbonylamino group (preferably a substituted or unsubstituted alkoxycarbonylamino group having 2 to 20 carbon atoms, e.g., methoxycarbonylamino, ethoxycarbonylamino, 2,2,2-trifluoroethoxycarbonylamino, and N-trifluoromethyl-methoxycarbonylamino), an aryloxycarbonylamino group (preferably a substituted or unsubstituted aryloxycarbonylamino group having 7 to 20 carbon atoms, e.g., phenoxycarbonylamino, and p-chlorophenoxycarbonylamino), a sulfamoylamino group (preferably a substituted or unsubstituted sulfamoylamino group having 0 to 20 carbon atoms, e.g., sulfamoylamino, and N,N-dimethylaminosulfonylamino), an alkyl- or aryl-sulfonylamino group (preferably, a substituted or unsubstituted alkylsulfonylamino group having 1 to 20 carbon atoms, and a substituted or unsubstituted arylsulfonylamino group having 6 to 20 carbon atoms, e.g., methylsulfonylamino, trifluoromethylsulfonylamino, butylsulfonylamino, and phenylsulfonylamino), a mercapto group, an alkylthio group (preferably a substituted or unsubstituted alkylthio group having 1 to 20 carbon atoms, e.g., methylthio, ethylthio, and 2,2,2-trifluoroethylthio), an arylthio group (preferably a substituted or unsubstituted arylthio group having 6 to 20 carbon atoms, e.g., phenylthio or p-chlorophenylthio, and pentafluorophenylthio), a sulfamoyl group (preferably a substituted or unsubstituted sulfamoyl group having 0 to 20 carbon atoms, e.g., N-ethylsulfamoyl, N,N-dimethylsulfamoyl, N,N-bis(2,2,2-trifluoroethyl)sulfamoyl, N-acetylsulfamoyl, and N-benzoylsulfamoyl), a sulfo group, a halosulfonyl group (e.g., chlorosulfonyl, and fluorosulfonyl), an alkyl- or arylsulfinyl group (preferably, a substituted or unsubstituted alkylsulfinyl group having 1 to 20 carbon atoms, and a substituted or unsubstituted arylsulfinyl group having 6 to 20 carbon atoms, e.g., methylsulfinyl, ethylsulfinyl, and phenylsulfinyl), an alkyl- or aryl-sulfonyl group (preferably, a substituted or unsubstituted alkylsulfonyl group having 1 to 20 carbon atoms, and a substituted or unsubstituted arylsulfonyl group having 6 to 20 carbon atoms, e.g., methylsulfonyl, trifluoromethylsulfonyl, ethylsulfonyl, and phenylsulfonyl), an acyl group (preferably, a substituted or unsubstituted alkylcarbonyl group having 1 to 20 carbon atoms, and a substituted or unsubstituted arylcarbonyl group having 7 to 20 carbon atoms, e.g., acetyl, trifluoroacetyl, pivaloyl, heptafluoropropionyl, benzoyl, and pentafluorobenzoyl), an aryloxycarbonyl group (preferably a substituted or unsubstituted aryloxycarbonyl group having 7 to 20 carbon atoms, e.g., phenoxycarbonyl and o-chlorophenoxycarbonyl), an alkoxycarbonyl group (preferably a substituted or unsubstituted alkoxycarbonyl group having 2 to 20 carbon atoms, e.g., methoxycarbonyl, ethoxycarbonyl, 2,2,2-trifluoroethoxycarbonyl, 2,2,3,3,4,4-hexafluorobutoxycarbonyl, and 2,2,3,3,4,4,4-heptafluorobutoxycarbonyl), a carbamoyl group (preferably a substituted or unsubstituted carbamoyl group having 1 to 30 carbon atoms, e.g., carbamoyl, N-methylcarbamoyl, N,N-dimethylcarbamoyl, and N,N-bis(2,2,2-trifluoroethyl)carbamoyl), and an imido group (preferably, N-succinimido, and N-phthalimido).

Among these, more preferable examples of the substituent include a fluorine atom, a chlorine atom, an alkyl group, a hydroxyl group, a halocarbonyl group, an alkoxy group, an acyloxy group, an alkoxycarbonyloxy group, a halosulfonyl group, an alkylsulfonyl group, an acyl group, and an alkoxycarbonyl group.

In formula (II), Lf represents a fluorine-containing alkylene chain obtained by converting at least one C—H bond in L in formula (I) with a C—F bond; and $X_{31}$, $X_{32}$, $X_{33}$, and $X_{34}$ have the same meanings as $X_{31}$, $X_{32}$, $X_{33}$, and $X_{34}$ in formula (1), respectively. Lf preferably represents a perfluoroalkylene group obtained by converting all C—H bonds in L with C—F bonds (, and by adding $F_2$ to the double bond in L, if any, to saturate each double bond).

In formula (III), Lf has the same meaning as the Lf in formula (II); and Xa and Xb each represent a halogen atom derived from $X_{32}$, $X_{33}$ or $X_{34}$.

In formula (IV), L has the same meaning as L in formula (1), and the preferable range thereof is also the same. $X_{35}$ represents a halogen atom other than a fluorine atom (e.g., chlorine, bromine, or iodine); and $X_{36}$ and $X_{37}$ each independently represent a halogen atom (e.g., fluorine, chlorine, bromine, or iodine). $X_{35}$ and $X_{36}$ each are preferably a chlorine atom; and $X_{37}$ is preferably a chlorine or fluorine atom.

In formula (V), Lf represents a fluorine-containing alkylene chain obtained by converting at least one C—H bond in L in formula (IV) with a C—F bond; and $X_{35}$, $X_{36}$ and $X_{37}$ have the same meanings as $X_{35}$, $X_{36}$, and $X_{37}$ in formula (IV).

In formula (VI), Lf has the same meaning as Lf in formula (V); and Xc represents a halogen atom derived from $X_{36}$ or $X_{37}$.

The compound represented by formula (I) or (IV) is fluorinated, to convert to a compound represented by formula (II) or (V).

The compounds represented by formula (I) or (IV) can be synthesized easily, according to, for example, the methods, as shown below, with reference to those described in U.S. Pat. No. 2,803,665, Tetrahedron Letters 42, 40, 2001, 6987–6990, Journal of Organometallic Chemistry, 71, 1974, 335–346, and Tetrahedron Letters, Vol. 39 (1998) 4071–4074.

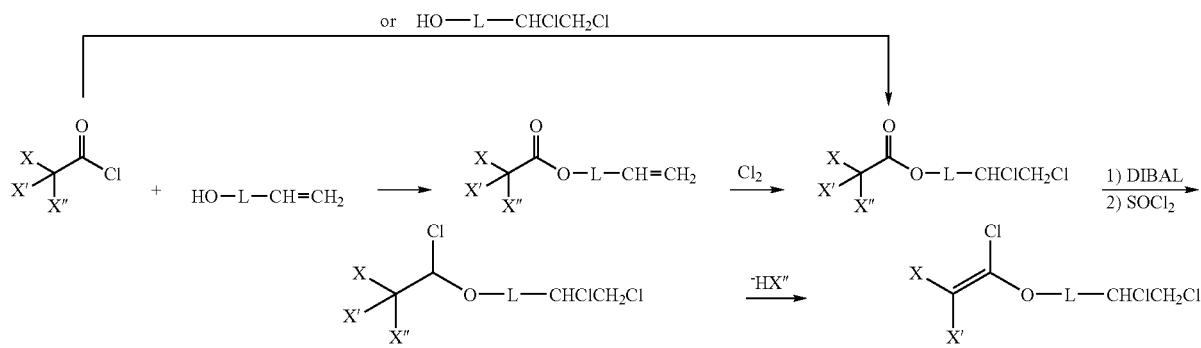

Other embodiments of the present invention include compounds of the formula $CClF=CFOCF_2CF_2CF=CF_2$, $CCl_2=CFOCF_2CF_2CF=CF_2$, or $CF_2=CFOCF(CF_2CF_3)$ $CF_2CF=CF_2$. These compounds of the formula $CClF=CFOCF_2CF_2CF=CF_2$, $CCl_2=CFOCF_2CF_2CF=CF_2$, or $CF_2=CFOCF(CF_2CF_3)$ $CF_2CF=CF_2$ can be prepared, according to the production method described above.

According to the method of the present invention, the fluorine-containing vinyl ether compound, in particular a perfluorovinyl ether compound, that is useful as a raw material for fluorine-containing resins, can be produced in a simple manner, from an inexpensive, readily available raw material, or from a more environment-friendly, readily available, and safe raw material.

Further, according to the method of the present invention, a fluorine-containing ω-vinyloxy-1-alkene compound, in particular a perfluoro(ω-vinyloxy-1-alkene), useful as a raw material for functional optical materials, can be produced in a simple manner in short or lesser steps, or further in a simple manner in short or lesser steps from an easily available, safe raw material. Further, according to the present invention, novel (chlorosubstituted)perfluoro(ω-vinyloxy-1-alkenes), e.g. chloroperfluoro(4-vinyloxy-1-butene), can be provided.

The present invention will be described in more detail based on the following examples, but the invention is not intended to be limited thereto.

EXAMPLES

Example 1

According to the following scheme, 1-(1-chloro-1,2,2,2-tetrafluoroethoxy)perfluorodecane was synthesized.

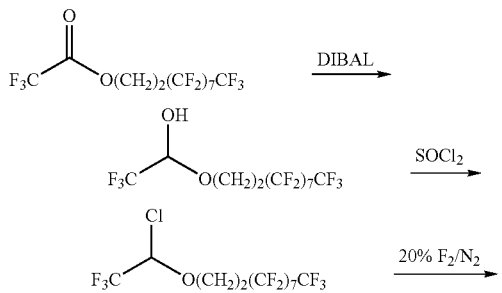

-continued

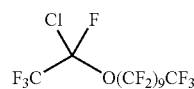

Synthesis of 10-(1-chloro-2,2,2-trifluoroethoxy)-1,1,1,2,2,3,3,4,4,5,5,6,6,7,7,8,8-heptadecafluorodecane A 1.0 M hexane solution (34 ml) of diisobutylaluminum hydride (hereinafter, referred to as DIBAL) was added, dropwise, at −70° C., to a tetrahydrofuran solution (60 ml) of 3,3,4,4,5,5,6,6,7,7,8,8,9,9,10,10,10-heptadecafluorodecyl trifluoroacetate ester (18.3 g) obtained by reaction of trifluoroacetic anhydride and 3,3,4,4,5,5,6,6,7,7,8,8,9,9,10,10,10-heptadecafluorodecanol, followed by stirring at −70 to −50° C. for 2 hours. The resultant reaction solution was allowed to warm gradually to 0° C., and 1-mol/L aqueous hydrochloric acid (5 ml) was added thereto, followed by stirring at the same temperature for 5 minutes. After extraction with ethyl acetate/1 mol/L-hydrochloric acid, the organic layer was washed with water and an aqueous sodium chloride solution, and then dried over magnesium sulfate. The solvent was concentrated under reduced pressure, to give crude 2,2,2-trifluoro-1-(3,3,4,4,5,5,6,6,7,7,8,8,9,9,10,10,10-heptadecafluorodecyloxy)ethanol. The resultant crude alcohol was dispersed in toluene (50 ml), and thionyl chloride (3.5 ml) and pyridine (4.0 ml) were added thereto, dropwise, at room temperature, followed by stirring for 3 hours. After the reaction solution was extracted with ethyl acetate/1 mol/L-aqueous hydrochloric acid, the organic layer was washed with water and an aqueous sodium chloride solution, dried over magnesium sulfate, and concentrated under reduced pressure. The concentrated residue was purified by column chromatography (developing solvent: ethyl acetate/hexane=1/9), to give 10-(1-chloro-2,2,2-trifluoroethoxy)-1,1,1,2,2,3,3,4,4,5,5,6,6,7,7,8,8-heptadecafluorodecane (11.9 g, 63%).

$^1$H NMR (300 MHz; solvent, CDCl$_3$; standard, TMS) 5.64 (q, J=3.3, 1H), 4.30–4.20 (m, 1H), 1H), 2.62–2.43 (m, 2H)

Synthesis of 1-(1-chloro-1,2,2,2-tetrafluoroethoxy) perfluorodecane

FC-72 (trade name, manufactured by Sumitomo 3M Limited, 175 ml) was placed in a 250-ml Teflon® reaction container, and kept at 25° C. A NaF pellet-packed layer, and a condenser held at –40° C. were set in series at the outlet of the reaction container, such that the liquid condensed in the condenser would be returned to the reaction container via a return line. Nitrogen gas was introduced at a rate of 30 ml/min for 1 hour, and a fluorine gas diluted to 20% with nitrogen gas (hereinafter, referred to simply as fluorine gas) was introduce at a rate of 100 ml/min for 45 min. While the fluorine gas was introduced at the same rate, thereto added were 10-(1-chloro-2,2,2-trifluoroethoxy)-1,1,1,2,2,3,3,4,4,5,5,6,6,7,7,8,8-heptadecafluorodecane (9.16 g, 15.8 mmol) at a rate of 0.041 ml/min, and a solution of hexafluorobenzene (0.3 g) in FC-72 (10 ml) at a rate of 0.083 ml/min. Then, were introduced the fluorine gas at the same rate for 10 minutes, and then nitrogen gas at a rate of 30 ml/min for 1 hour. The solvent was concentrated, and further distilled off under reduced pressure, to give 1-(1-chloro-1,2,2,2-tetrafluoroethoxy)perfluorodecane 9.26 g (87%, purity by gas chromatography 95.2%).

$^{19}$F-NMR (282.24 MHz; solvent, CDCl$_3$; standard, CFCl$_3$)-80.55 (dd, J=23.42, 9.60 Hz, 1F), –J=9.74 Hz, 3F), –83.24 (ddt, J=144.56, 23.42, 9.60, 1F), –84.70 (ddt, J=144.56, 9.60, 9.60, 1F), –86.25 (s, 3F), –122.27 (brs, 8F), –122.57 (brs, 2F), –123.19 (brs, 2F), –125.98 (brs, 2F), –126.68 (brs, 2F); b.p. 112° C./35 mmHg The thus-obtained 1-(1-chloro-1,2,2,2-tetrafluoroethoxy) perfluorodecane can be converted to perfluoro(decyl vinyl ether), via de-chlorofluorination in a similar manner to the method described in JP-A-11-335309.

Example 2

According to the following scheme, i-(1,2-dichloro-1,2, 2-trifluoroethoxy)perfluorodecane was synthesized.

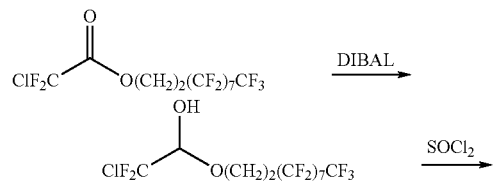

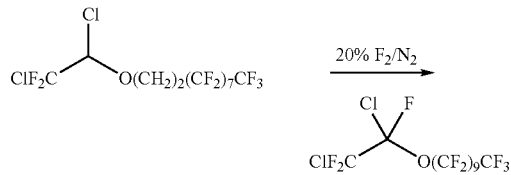

Synthesis of 10-(1,2-dichloro-2,2-difluoroethoxy)-1, 1,1,2,2,3,3,4,4,5,5,6,6,7,7,8,8-heptadecafluorodecane A 11.0M hexane solution (34 ml) of DIBAL was added, dropwise, at –70° C., to a tetrahydrofuran solution (60 ml) of 3,3,4,4,5,5,6,6,7,7,8,8,9,9,10,10,10-heptadecafluorodecyl chlorodifluoroacetate ester (18.8 g) obtained by DCC condensation of chlorodifluoroacetic acid and 3,3,4,4,5,5,6,6,7,7,8,8,9,9,10,10,10-heptadecafluorodecanol, followed by stirring at –70 to –60° C. for 2.5 hours. The reaction solution was allowed to warm gradually to 0° C., and then 1-mol/L aqueous hydrochloric acid (3 ml) was added thereto, followed by stirring at the same temperature for 5 minutes. After extraction with ethyl acetate/1 mol/L-aqueous hydrochloric acid, the organic layer was washed with water and an aqueous sodium chloride solution, and dried over magnesium sulfate. Concentration of the solvent under reduced pressure gave crude 2-chloro-2,2-difluoro-1-(3,3,4,4,5,5,6,6,7,7,8,8,9,9,10,10,10-heptadecafluorodecyloxy)ethanol.

The crude alcohol was dispersed in toluene (50 ml), and thionyl chloride (3.5 ml) and pyridine (4.0 ml) were added dropwise thereto at room temperature, followed by stirring for 3 hours. After extraction of the reaction solution with ethyl acetate/1 mol/L-aqueous hydrochloric acid, the organic layer was washed with water and an aqueous sodium chloride solution, dried over magnesium sulfate, and concentrated under reduced pressure. The concentrated residue was purified by column chromatography (developing solvent: ethyl acetate/hexane=1/9), to give 10-(1,2-dichloro-2, 2-difluoroethoxy)-1,1,1,2,2,3,3,4,4,5,5,6,6,7,7,8,8-heptadecafluorodecane (10.1 g, 52%).

$^1$H NMR (400 MHz; solvent, CDCl$_3$; standard, TMS) 5.64 (dd, J=7.3, 1.5, 1H), 4.32-4.21 (m, 1H),4.00-3.89 (m, 1H), 2.70–2.46 (m, 2H)

Synthesis of 1-(1,2-dichloro-1,2,2-trifluoroethoxy) perfluorodecane

FC-72 (175 ml) was placed in a 250-ml Teflon® reaction container, and kept at 25° C. A NaF pellet-packed layer and a condenser held at –40° C. were set in series at the outlet of the reaction container, such that the liquid condensed in the condenser would be returned to the reaction container via a return line. Nitrogen gas was introduced thereto at a rate of 30 ml/min for 1 hour, and then the fluorine gas was introduced at a rate of 100 ml/min for 45 minutes. While introducing the fluorine gas at the same rate, 10-(1,2-dichloro-2,2-difluoroethoxy)-1,1,1,2,2,3,3,4,4,5,5,6,6,7,7,8, 8-heptadecafluorodecane (9.27 g, 15.5 mmol) was added at a rate of 0.042 ml/min, and then a FC-72 solution (10 ml) of hexafluorobenzene (0.38 g) was added at a rate of 0.083 ml/min. Then, the fluorine gas was introduced at the same rate for 10 minutes, and nitrogen gas was introduced at a rate of 30 ml/min for 1 hour. Concentration of the solvent, and distillation under reduced pressure gave I-(1,2-dichloro-1,2, 2-trifluoroethoxy)perfluorodecane 7.48 g (70%, purity by gas chromatography 78.11%, the primary impurity was 1-(1-chloro-1,2,2,2-tetrafluoroethoxy)perfluorodecane.).

$^{19}$F-NMR (282.24 MHz; solvent, CDCl$_3$; standard, CFCl$_3$)-71.20 (d, J=5.93 Hz, 1F), −71.30 (d, J=7.90 Hz, 1F), −77.20 (dddd, J=23.42, 9.74, 7.90, 5.93, 1F), −81.30 (t, J=10.72, 3F), −82.69 (ddt, J=144.05, 23.42, 9.60, 1F), −84.09 (ddt, J=144.65, 9.74, 9.60, 1F), −122.29 (brs, 10F), −123.21 (brs, 2F), −125.93 (brs, 2F), −126.64 (brs, 2F); and b.p. 110–120° C./28 mmHg The thus-obtained 1-(1,2-dichloro-1,2,2-trifluoroethoxy) perfluorodecane can be converted to perfluoro(decyl vinyl ether), by dechlorination according to the method in a similar manner to Example 4 described below.

Example 3

According to the following scheme, i-(1,2,2-trichloro-1,2-difluoroethoxy)perfluorodecane was synthesized.

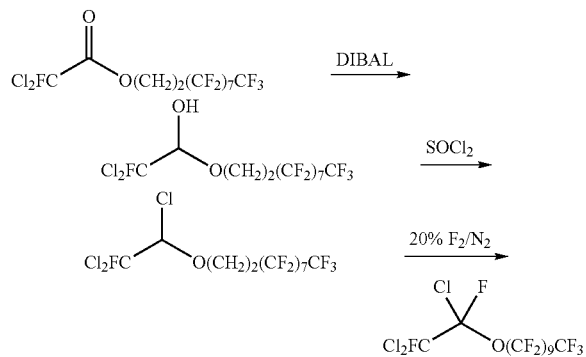

Synthesis of 10-(1,2,2-trichloro-2-fluoroethoxy)-1,1,1,2,2,3,3,4,4,5,5,6,6,7,7,8,8-heptadecafluorodecane A 1.0M hexane solution of DIBAL (24 ml) was added dropwise at −70° C., to a tetrahydrofuran solution (50 ml) of 3,3,4,4,5,5,6,6,7,7,8,8,9,9,10,10,10-heptadecafluorodecyl dichlorofluoroacetate ester (13.6 g) obtained by transesterification of methyl dichlorofluoroacetate with 3,3,4,4,5,5,6,6,7,7,8,8,9,9,10,10,10-heptadecafluorodecanol, followed by stirring at −70 to −50° C. for 1 hour. The reaction solution was allowed to warm gradually to 0° C., and then 1-mol/L aqueous hydrochloric acid (5 ml) was added thereto, followed by stirring at the same temperature for 5 minutes. After extraction with ethyl acetate/1 mol/L-aqueous hydrochloric acid, the organic layer was washed with water and an aqueous sodium chloride solution, and dried over magnesium sulfate. Concentration of the solvent under reduced pressure gave crude 2,2-dichloro-2-fluoro-1-(3,3,4,4,5,5,6,6,7,7,8,8,9,9,10,10,10-heptadecafluorodecyloxy)ethanol. The crude alcohol was dispersed in toluene (40 ml), and thionyl chloride (2.5 ml) and pyridine (2.8 ml) were added dropwise at room temperature, followed by stirring for 3 hours. After extraction of the reaction solution with ethyl acetate/1 mol/L-aqueous hydrochloric acid, the organic layer was washed with water and an aqueous sodium chloride solution, dried over magnesium sulfate, and concentrated under reduced pressure. The concentrated residue was purified by column chromatography (developing solvent: ethyl acetate/hexane=1/9), to give 10-(1,2,2-trichloro-2-fluoroethoxy)-1,1,1,2,2,3,3,4,4,5,5,6,6,7,7,8,8-heptadecafluorodecane (10.1 g, 72%).

$^1$H NMR (CDCl$_3$) 5.72 (d, J=3.5, 1H), 4.35–4.21 (m, 1H), 4.01–3.90 (m, 1H), 2.70–2.43 (m, 2H)

Synthesis of 1-(1,2,2-trichloro-1,2-difluoroethoxy) perfluorodecane

FC-72 (175 ml) was placed in a 250-ml Teflon® reaction container, and kept at 25° C. A NaF pellet-packed layer and a condenser held at −40° C. were set in series at the outlet of the reaction container, such that the liquid condensed in the condenser would be returned to the reaction container via a return line. Nitrogen gas was introduced at a rate of 30 ml/min for 1 hour, and then the fluorine gas was introduced at a rate of 100 m/min for 45 minutes. While introducing the fluorine gas at the same rate, 10-(1,2,2-trichloro-2-fluoroethoxy)-1,1,1,2,2,3,3,4,4,5,5,6,6,7,7,8,8-heptadecafluorodecane (9.07 g, 14.78 mmol) was added at a rate of 0.044 ml/min, and then an FC-72 solution (10 ml) of hexafluorobenzene (0.57 g) was added at a rate of 0.083 ml/min. The fluorine gas was introduced at the same rate additionally for 10 minutes, and nitrogen gas was introduced at a rate of 30 m/min for 1 hour. Concentration of the solvent, and distillation under reduced pressure gave 1-(1,2,2-trichloro-1,2-difluoroethoxy)perfluorodecane 8.53 g (82%, purity by gas chromatography 80.9%, the primary impurity was 1-(1,2-dichloro-1,2,2-trifluoroethoxy)perfluorodecane).).

$^{19}$F-NMR (282.24 MHz; solvent, CDCl$_3$; standard, CFCl$_3$)-72.37 (d, J=11.85, 1F), −74.18 (ddd, J=22.44, 11.85, 8.75, 1F), −81.36 (t, J=9.74, 3F), −83.12 (ddt, J=143.66, 22.44, 9.97, 1F), −85.41 (ddt, J=143.66, 8.75, 9.97, 1F), −122.26 (brs, 10F), −123.20 (brs, 2F), −125.90 (brs, 2F), −126.64 (brs, 2F); and b.p. 107° C./5 mmHg The thus-obtained 1-(1,2,2-trichloro-1,2-difluoroethoxy) perfluorodecane can be converted to a corresponding vinyl ether (2-chloro-1,2-difluoro-1-perfluorodecyloxyethene), by dechlorination, according to the method similar to that in Example 4 described below.

Example 4

According to the following scheme, CClF=CFOCF$_2$CF$_2$CF=CF$_2$ was synthesized.

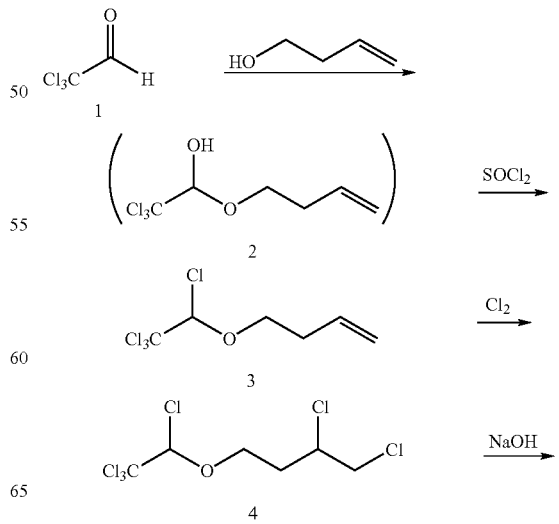

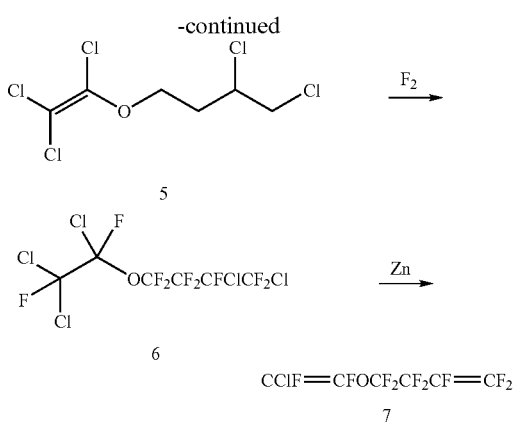

CClF=CFOCF₂CF₂CF=CF₂

7

Synthesis of Compound 3

Chloral (25.5 g) was added dropwise at 16° C. to 3-buten-1-ol (13.1 g), followed by stirring for 30 minutes. Toluene (20 ml) was added to the solution, and thionyl chloride (14.9 ml) and pyridine (18.2 ml) were added dropwise thereto at 10° C., followed by stirring at room temperature for 2 hours and 30 minutes. After filtration of the solid matter, the filtrate was extracted with ethyl acetate/sodium bicarbonate. The organic layer was washed with water and an aqueous sodium chloride solution, and dried over magnesium sulfate. After concentration under reduced pressure, the residue was purified by column chromatography (developing solvent: hexane), to give Compound 3 (29.6 g, 72%).

¹H NMR (300 MHz; solvent, CDCl₃; standard, TMS) 5.91–5.75 (m, 1H), 5.78 (s, 1H), 5.17 (d, J=17.5, 1H), 5.11 (d, J=9.0, 1H), 4.08 (dt, J=10.5, 7.5, 1H), 3.78 (dt, J=10.5, 7.5, 1H), 2.48 (dt, J=7.9, 5.0, 2H)

Synthesis of Compound 4

Chlorine gas was introduced slowly to Compound 3 (25.1 g) at 5° C. (such that the temperature would not exceed 15° C.), until the system turned pale yellow. Nitrogen gas was introduced into the reaction system until the system became colorless, and then, the residue was purified by column chromatography (developing solvent: hexane), to give Compound 4 (24.2 g, 75%).

¹H NMR (300 MHz; solvent, CDCl₃; standard, TMS) [5.77 (s), 5.75 (s), 1H], 4.40–4.18 (m, 2H), 4.00–3.68 (m, 3H), 2.51–2.39 (m, 1H), 2.12–1.96 (m, 1H)

Synthesis of Compound 5

An aqueous solution of NaOH (3.0 g)/water (20 ml) was added dropwise to an ethanol solution (100 ml) of Compound 4 (15.4 g) at 5° C., and the resultant mixture was stirred at room temperature for 3 hours and 30 minutes, and then poured into ethyl acetate (300 ml)/water (300 ml). After separation, the organic layer was washed with an aqueous sodium chloride solution, and dried over magnesium sulfate. After concentration under reduced pressure, the residue was purified by column chromatography (developing solvent: hexane), to give Compound 5 (8.3 g, 61%).

¹H NMR (400 MHz; solvent, CDCl₃; standard, TMS) 4.39–4.28 (m, 1H), 4.28–4.12 (m, 2H) J=16.8, 7.6, 1H), 3.72 (dd, J=16.8, 8.4, 1H), 2.52–2.39 (m, 1H), 2.10–1.93 (m, 1H)

Synthesis of Compound 6

FC-72 (175 ml) was placed in a 250-ml Teflon® reaction container, and kept at 0° C. A NaF pellet-packed layer and a condenser held at −40° C. were set in series at the outlet of the reaction container, such that the liquid condensed in the condenser would be returned to the reaction container via a return line. Nitrogen gas was introduced at a rate of 30 ml/min for 1 hour, and the fluorine gas was introduced at a rate of 100 ml/min for 45 minutes. While introducing the fluorine gas at the same rate, a trichlorofluoromethane solution (10 ml) of Compound 5 (1.02 g) and hexane (0.021 g) was added at a rate of 0.22 ml/min, and then an FC-72 solution (10 ml) of hexafluorobenzene (0.3 g) was added at a rate of 0.083 ml/min. Then, the fluorine gas was introduced at the same rate additionally for 10 minutes, and nitrogen gas was introduced at a rate of 30 ml/min for 1 hour. Concentration of the solvent, and distillation under reduced pressure gave Compound 6 (0.74 g, 46%, purity by gas chromatography 64%).

Synthesis of CClF=CFOCF₂CF₂CF=CF₂

Compound 6 (1.10 g) was added dropwise to a dispersion of zinc (1.32 g) in DMF (5 ml) at 60° C., followed by stirring for 2 hours. Distillation of the reaction solution under reduced pressure, and further distillation of the resultant crude matter under atmospheric pressure for purification gave CClF=CFOCF₂CF₂CF=CF₂ (0.43 g, 62%). It was identified by ¹⁹F-NMR that the resultant compound was a mixture of cis- and trans-isomers at approximately 6:4.

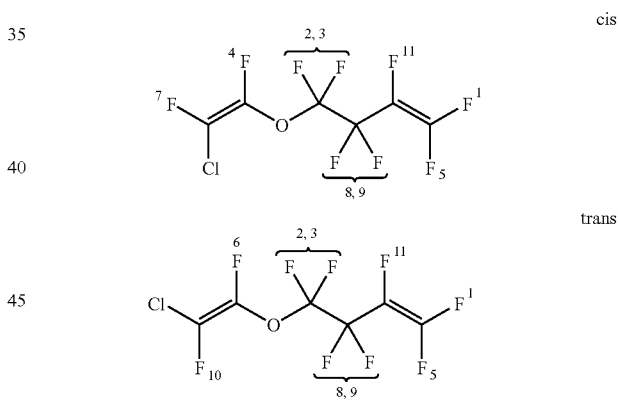

¹⁹F-NMR (600 MHz; solvent, CDCl₃; standard, CFCl₃) 1, −88 to −89; 2, −89.0; 3, −89.2; 4, −102.8; 5, −105 to −106; 6, −118 to −119; 7, −119 to −120; 8, −122.0; 9, −122.1; 10, −128; 11, −190.1

Example 5

According to the following scheme, CClF=CFOCF₂CF₂CF=CF₂ was synthesized.

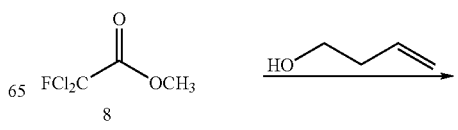

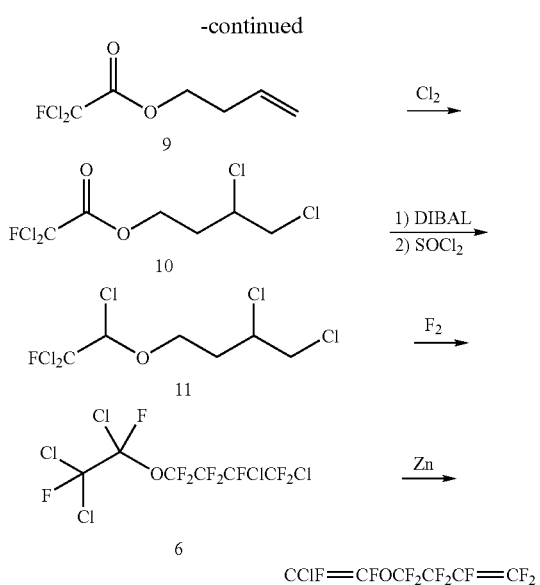

Synthesis of Compound 9

To a mixture of 3-buten-1-ol (18.0 g) and methyl dichlorofluoroacetate (8) (33.5 g) synthesized according to the method described in Chem. Lett., 1987, 1145–1148, was added conc. sulfuric acid (1 ml), followed by stirring at 85° C. for 3 hours. The reaction solution was poured into dichloromethane (200 ml)/aqueous sodium bicarbonate solution (200 ml), and after separation, the organic layer was washed with water and an aqueous saturated sodium chloride solution, and then dried over magnesium sulfate. Concentration of the solvent, and distillation under reduced pressure gave Compound 9 (31.0 g, 74%).

$^1$H NMR (300 MHz; solvent, CDCl$_3$; standard, TMS) 5.80 (m, 1H), 5.21 (s, 1H), 5.18–5.12 (m, 1H), 4.41 (t, J=6.2, 2H), 2.50 (q, J=6.2, 2H)

Synthesis of Compound 10

Chlorine gas was introduced slowly to Compound 9 (25.1 g) at 5° C. (such that the temperature would not exceed 10° C.), until the system turned pale yellow. Nitrogen gas was introduced into the reaction system until it became colorless, and then, the residue was purified by column chromatography (developing solvent: hexane/ethyl acetate=9:1), to give Compound 0.10 (18.8 g, 55%).

$^1$H NMR (400 MHz; solvent, CDCl$_3$; standard, TMS) 4.67–4.50 (m, 2H), 4.28–4.12 (m, 1H) 3.90–3.65 (m, 2H), 2.60–2.48 (m, 1H), 2.18–2.05 (m, 1H)

Synthesis of Compound 11

A 1.0M hexane solution (68 ml) of DIBAL was added, dropwise, to a tetrahydrofuran solution (60 ml) of Compound 10 (17.7 g) at −70° C., followed by stirring at −70 to −50° C. for 2.5 hours. The reaction solution was allowed to warm gradually to 0° C., then 1-mol/L aqueous hydrochloric acid (3 ml) was added thereto, followed by stirring at the same temperature for 5 minutes. After extraction with ethyl acetate/1 mol/L-aqueous hydrochloric acid, the organic layer was washed with water and an aqueous sodium chloride solution, and dried over magnesium sulfate. The solvent was concentrated under reduced pressure, and the residue was dispersed in toluene (40 ml), then thionyl chloride (4.7 ml) and pyridine (5.3 ml) were added, dropwise, at room temperature, followed by stirring for 3 hours. After extraction of the reaction solution with ethyl acetate/1 mol/L-aqueous hydrochloric acid, the organic layer was washed with an aqueous sodium bicarbonate solution, water, and an aqueous sodium chloride solution, followed by drying over magnesium sulfate, and the resultant was concentrated under reduced pressure. The concentrated residue was purified by column chromatography (developing solvent: ethyl acetate/hexane=1/9), to give Compound 11 (6.80 g, 36%).

$^1$H NMR (400 MHz; solvent, CDCl$_3$; standard, TMS) 5.74–5.69 (m, 1H), 4.35–4.18 (m, 2H) 3.94–3.68 (m, 3H), 2.50–2.39 (m, 1H), 2.10–1.95 (m, 1H)

Synthesis of Compound 6

FC-72 (175 ml) was placed in a 250-ml Teflon® reaction container, and kept at 0° C. A NaF pellet-packed layer and a condenser held at −40° C. were set in series at the outlet of the reaction container, such that the liquid condensed in the condenser would be returned to the reaction container via a return line. Nitrogen gas was introduced at a rate of 30 ml/min for 1 hour, and then the fluorine gas was introduced at a rate of 100 ml/min for 45 minutes. While introducing the fluorine gas at the same rate, a liquid mixture of Compound 11 (5.1 g) and hexane (0.086 g) was added at a rate of 0.02 g/min, and a FC-72 solution (10 ml) of hexafluorobenzene (1.74 g) was added at a rate of 0.065 mL/min. Then, the fluorine gas was introduced at the same rate additionally for 10 minutes, and nitrogen gas was introduced at a rate of 30 ml/min for 1 hour. Concentration of the solvent, and further concentration under reduced pressure gave Compound 6 (4.8 g, 63%, GC purity 78%, b.p. 100° C./45 mmHg). CClF=CFOCF$_2$CF$_2$CF=CF$_2$ was prepared from the thus-obtained Compound 6 in a similar manner to Example 4. It was identified from $^{19}$F-NMR that the compound was a mixture of cis-/trans-isomers similar to Compound 6 synthesized in Example 4.

Example 6

According to the following scheme, CF$_2$=CFOCF$_2$CF$_2$CF=CF$_2$ was synthesized.

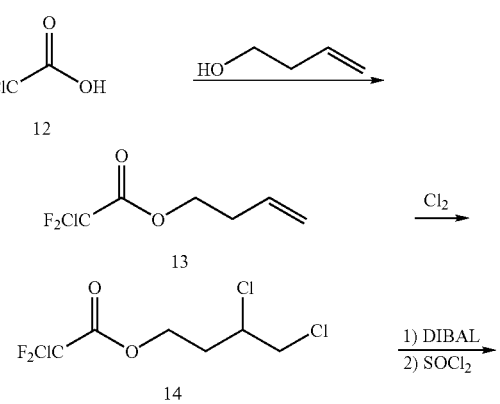

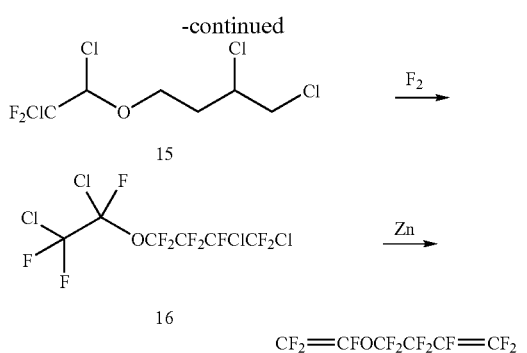

$CF_2$=$CFOCF_2CF_2CF$=$CF_2$

17

Synthesis of Compound 13 p-Toluenesulfonic acid monohydrate (4.0 g) was added to a mixture of chlorodifluoroacetic acid (12) (58.0 g), 3-buten-1-ol (30.5 g) and hexane (100 ml), and the resultant mixture was heated under reflux for 3 hours, while conducting dehydration. After the reaction mixture was extracted with hexane/aqueous sodium bicarbonate solution, the organic layer was washed with water and an aqueous saturated sodium chloride solution, and then dried over magnesium sulfate. Concentration of the solvent, and distillation under reduced pressure gave Compound 13 (66.0 g, 85%).

$^1$H NMR (400 MHz; solvent, CDCl$_3$; standard, TMS) 5.83–5.73 (m, 1H), 5.19 (s, 1H), 5.18–5.13 (m, 1H), 4.40 (t, J=6.3, 2H), 2.50 (q, J=6.3, 2H)

Synthesis of Compound 14

Chlorine gas was introduced slowly to Compound 13 (20 g) at 5° C. (such that the temperature would not exceed 10° C.), until the system turned pale yellow. Nitrogen gas was introduced into the reaction system until it became colorless, and then, the residue was purified by column chromatography (developing solvent: hexane/ethyl acetate=9:1), to give Compound 14 (23.3 g, 84%).

$^1$H NMR (400 MHz; solvent, CDCl$_3$; standard, TMS) 4.65–4.50 (m, 2H), 4.22–4.12 (m, 1H) 3.84 (dd, J=11.8, 4.7, 1H), 3.70 (dd, J=11.8, 7.8, 1H), 2.59–2.48 (m, 1H), 2.19–2.06 (m, 1H)

Synthesis of Compound 15

A 1.0M hexane solution (70 ml) of DIBAL was added, dropwise, at −70° C., to a tetrahydrofuran solution (60 ml) of Compound 14 (17.0 g), followed by stirring at −70 to −50° C. for 2.5 hours. The reaction solution was allowed to warm gradually to 0° C., then 1-mol/L aqueous hydrochloric acid (20 ml) was added thereto, followed by stirring at the same temperature for 5 minutes. After extraction with ethyl acetate/1 mol/L-aqueous hydrochloric acid, the organic layer was washed with water and an aqueous sodium chloride solution, and dried over magnesium sulfate. The solvent was concentrated under reduced pressure, the residue was dispersed in toluene (50 ml), and thionyl chloride (7 ml) and pyridine (8 ml) were added dropwise thereto, under cooling on ice, followed by stirring for 3 hours. After extraction of the reaction solution with ethyl acetate/1 mol/L-aqueous hydrochloric acid, the organic layer was washed with an aqueous sodium bicarbonate solution, water, and then an aqueous sodium chloride solution, followed by drying over magnesium sulfate, and the resultant was concentrated under reduced pressure. The concentrated residue was purified by column chromatography (developing solvent: ethyl acetate/hexane=1/9), to give Compound 15 (14.9 g, 81%).

$^1$H NMR (400 MHz; solvent, CDCl$_3$; standard, TMS) 5.69–5.60 (m, 1H), 4.32–4.10 (m, 2H) 3.92–3.67 (m, 3H), 2.50–2.38 (m, 1H), 2.11–1.93 (m, 1H)

Synthesis of Compound 16

FC-72 (175 ml) was placed in a 250-ml Teflon® reaction container, and kept at 0° C. A NaF pellet-packed layer and a condenser held at −40° C. were set in series at the outlet of the reaction container, such that the liquid condensed in the condenser would be returned to the reaction container via a return line.

Nitrogen gas was introduced at a rate of 30 ml/min for 1 hour, and then the fluorine gas was introduced at a rate of 100 ml/min for 45 minutes. While introducing the fluorine gas at the same rate, a liquid mixture of Compound 15 (7.5 g) and hexane (0.13 g) was added at a rate of 0.019 g/min, and then an FC-72 solution (10 ml) of hexafluorobenzene (0.4 g) was added at a rate of 0.058 ml/min. Then, the fluorine gas was introduced at the same rate additionally for 10 minutes, and nitrogen gas was introduced at a rate of 30 ml/min for 1 hour. Concentration of the solvent, and further concentration under reduced pressure gave Compound 16 (8.7 g, 76%, purity by gas chromatography 84%, b.p. 100° C./85 mmHg).

Synthesis of $CF_2$=$CFOCF_2CF_2CF$=$CF_2$

Compound 16 (5.7 g) was added, dropwise, to a DMF dispersion (25 ml) of zinc (7.0 g) at 60° C., followed by stirring for 2 hours. Distillation of the reaction solution under reduced pressure, and the 40 subsequent distillation purification under atmospheric pressure of the crude material thus obtained gave pure $CF_2$=$CFOCF_2CF_2CF$=$CF_2$ (1.8 g, 48%).

$^{19}$F-NMR (600 MHz; solvent, CDCl$_3$; standard, CFCl$_3$) agreed well with the literature values (e.g., JP-A-1-143843)

Example 7

According to the following scheme, $CF_2$=$CFOCF$ $(CF_2CF_3)CF_2CF$=$CF_2$ was synthesized.

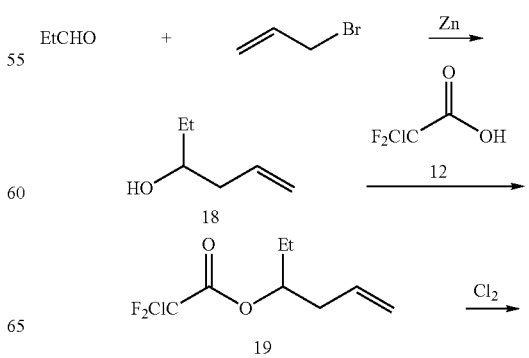

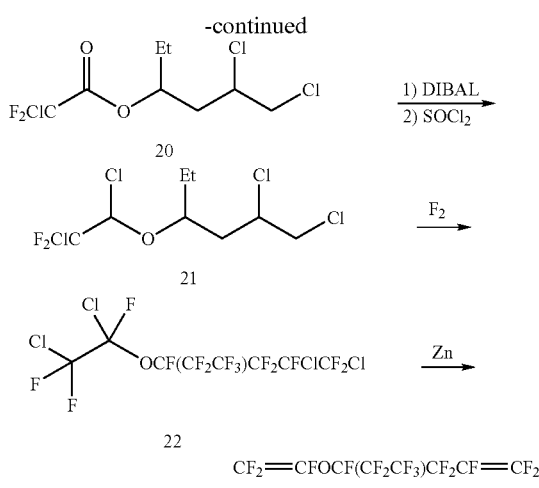

Synthesis of Compound 18

Unactivated zinc powder (47 g), water (75 ml), propionaldehyde (23 mL), and allyl bromide (41.5 mL) were placed in a reactor, and the resultant mixture was cooled on an ice bath, to bring an internal temperature to 5° C., while stirring. Then, concentrated hydrochloric acid (an aqueous solution containing hydrogen chloride at 35%) (15 mL) was added, dropwise, over 2 hours, while the internal temperature was controlled to 5 to 20° C. After removal of the ice bath, the reaction solution was stirred additionally for 1 hour, and then filtered, and the filtrate was saturated with sodium chloride, and the resultant mixture was extracted twice with hexane. GLC analysis showed that Compound 18 was contained in the hexane in an amount of 293.3 mmol (yield 92%).

$^1$H NMR (300 MHz; solvent, CDCl$_3$ standard: TMS) 5.78–5.89 (m, 1H), 5.15 (m, 1H), 5.12 (m, 1H), 3.58 (m, 1H), 2.30 (m, 1H), 2.15 (m, 1H), 1.75 (brs, 1H), 1.50 (m, 2H), 0.96 (t, J=7.40 Hz, 3H)

Synthesis of Compound 19

The thus-obtained hexane solution containing Compound 18 was diluted with hexane to a total volume of 100 mL, followed by heating under reflux at external temperature 120° C. Thereto, a hexane solution (50 mL) containing chlorodifluoroacetic acid (12) (35.3 mL) and p-toluenesulfonic acid monohydrate (0.53 g) was added, dropwise, over 1 hour. Water generated during the reaction was distilled off. After the completion of said dropwise addition, the mixture was heated additionally for 4 hours, and then stood to cool. The resultant reaction solution was washed with water, and then with an aqueous saturated sodium bicarbonate solution. Distillation of the reaction solution gave Compound 19 (38.1 g, purity by gas chromatography 97%).

$^1$H NMR (300 MHz; solvent, CDCl$_3$ standard: TMS) 5.70–5.79 (m, 1H), 5.00–5.16 (m, 3H), 2.42 (m, 2H), 1.72 (dt, J=14.1 Hz, 2H), 0.96 (t, J=7.35 Hz, 3H) $^{19}$F NMR (282.4 MHz, CDCl$_3$)–64.3 (s, 2F)

Synthesis of Compound 20

Chlorine gas was introduced slowly to Compound 19 (117.5 mmol, 25 g) at –10° C. (such that the temperature would not exceed 10° C.), until no heat generation in the system was observed. After introduction of nitrogen gas, purification of the reaction product by column chromatography (developing solvent: ethyl acetate/hexane=1/100), and then distillation gave Compound 20 (18.6 g, yield 56%, purity by gas chromatography 93%).

$^1$H NMR (300 MHz; solvent, CDCl$_3$ standard: TMS) 5.15–5.36 (m, 1H), 4.05–4.10 (m, 1H), 3.80–3.85 (m, 1H), 3.64–3.70 (m, 1H), 2.39–2.45 (m, 1H), 2.19–2.21 (m, 1H), 1.91–2.00 (m, 1H), 1.74–1.85 (m, 2H), 0.97 (t, J=7.5 Hz, 3H) $^{19}$F NMR (282.4 MHz, CDCl$_3$)–64.6, –64.8 (brs, 2F)

Synthesis of Compound 21

A 0.94M hexane solution (234 mL) of DIBAL was added, dropwise, to a diethyl ether solution (100 mL) of Compound 20 (50 g) at –70° C., followed by stirring at –70 to –50° C. for 2 hours. The reaction solution was allowed to warm gradually to 0° C., then the reaction solution was added, dropwise, into a mixture of ice and 1-mol/L aqueous hydrochloric acid (200 ml), followed by stirring at the same temperature for 30 minutes. After extraction with ethyl acetate/1 mol/L-aqueous hydrochloric acid, the organic layer was washed with water and an aqueous sodium chloride solution, and dried over magnesium sulfate. The solvent was concentrated under reduced pressure, the residue was dispersed in toluene (200 ml), and thionyl chloride (40 ml) and pyridine (40 ml) were added, dropwise, thereto while the mixture was ice-cooled, followed by stirring for 3 hours. After extraction of the reaction solution with ethyl acetate/1 mol/L-aqueous hydrochloric acid, the organic layer was washed with an aqueous sodium bicarbonate solution, water, and then an aqueous sodium chloride solution, followed by drying over magnesium sulfate, and the resultant was concentrated under reduced pressure. Purification of the concentrated residue by column chromatography (developing solvent: ethyl acetate/hexane=1/100) gave Compound 21 (33.4 g, 62%).

$^1$H NMR (400 MHz; solvent, CDCl$_3$; standard, TMS) 5.70–5.76, 5.80–5.84 (m, 1H), 4.02–4.34 (m, 2H), 3.65–3.88 (m, 2H), 1.64–1.88, 1.95–2.09, 2.18–2.31 (m, 4H), 0.95–1.09 (m, 3H)

$^{19}$F NMR (282.4 MHz, CDCl$_3$)–63.0 (m, 1H), –67.5 (m, 1F)

Synthesis of Compound 22

In a 500-ml Teflon® reaction container, FC-72 (350 ml) was placed, and kept at –10° C. At the outlet of the reaction container, an NaF pellet-packed layer and a condenser held at –40° C. were set in series, such that the liquid condensed in the condenser would be returned to the reaction container via a return line. Nitrogen gas was introduced at a rate of 30 ml/min for 1 hour, and then the fluorine gas was introduced at a rate of 300 ml/min for 10 minutes. While introducing the fluorine gas at the same rate, a liquid mixture of Compound 21 (10 g) and hexane (0.24 g) was added at a rate of 0.063 g/min, and then an FC-72 solution (20 ml) of hexafluorobenzene (10 g) was added at a rate of 0.055 ml/min. Then, the fluorine gas was introduced at the same rate additionally for 10 minutes, and nitrogen gas was introduced at a rate of 30 ml/min for 1 hour. Concentration of the solvent, and further concentration under reduced pressure gave Compound 22 (7.9 g, 46%, purity by gas chromatography 88%, b.p. 115° C./75 mmHg).

Synthesis of $CF_2$=$CFOCF(CF_2CF_3)CF_2CF$=$CF_2$

Compound 22 (5.0 g) was added, dropwise, at 80° C., to a DMF dispersion (25 ml) of zinc (5.0 g), followed by stirring for 0.5 hour. Distillation of the reaction solution under reduced pressure, and the subsequent distillation purification of the thus-obtained crude material under atmospheric pressure gave pure $CF_2$=$CFOCF(CF_2CF_3)CF_2CF$=$CF_2$ (1.3 g, 36%).

$^{19}$F-NMR (282.4 MHz; solvent, $CDCl_3$)-80.2 (d, J=6.5 Hz, 3F), −87.3 to 87.6 (m, 1F), −103.3 to 104.1 (m, 1F), −113.4 to −113.9 (m, 1F), −114.5 to −117.8 (m, 2F), −120.6 to −125.7 (m, 2F), −132.3 to −132.9 (m, 1F), −137.2 to −137.4 (m, 1F), −187.4 to −188.0 (m, 1F)

Example 8

According to the following scheme, $CCl_2$=$CFOCF_2CF_2CF$=$CF_2$ was synthesized.

Synthesis of Compound 24

In a 500-ml Teflon® reaction container, FC-72 (350 ml) was placed, and kept at −10° C. A NaF pellet-packed layer and a condenser held at −40° C. were set in series at the outlet of the reaction container, such that the liquid condensed in the condenser would be returned to the reaction container via a return line. Nitrogen gas was introduced at a rate of 30 ml/min for 1 hour, and then the fluorine gas was introduced at a rate of 300 ml/min for 10 minutes. While introducing the fluorine gas at the same rate, a liquid mixture of Compound 4 (26.5 g) and hexane (0.48 g) was added at a rate of 0.073 g/min, and then an FC-72 solution (30 ml) of hexafluorobenzene (6 g) was added at a rate of 0.22 ml/min. Then, the fluorine gas was introduced at the same rate additionally for 10 minutes, and nitrogen gas was introduced at a rate of 30 m/min for 1 hour. Concentration of the solvent, and further concentration under reduced pressure gave Compound 24 (24.2 g, yield 62%, purity by gas chromatography 85%).

Synthesis of $CCl_2$=$CFOCF_2CF_2CF$=$CF_2$

Compound 24 (10 g) was added, dropwise, at 80° C., to a triglyme dispersion (50 ml) of zinc (11.5 g), followed by stirring at 80° C. for 0.5 hour. Distillation of the reaction solution under reduced pressure, and the subsequent distillation purification of the thus-obtained crude material under atmospheric pressure gave pure $CCl_2$=$CFOCF_2CF_2CF$=$CF_2$ (2.7 g, 39%).

$^{19}$F-NMR (282.4 MHz; solvent, $CDCl_3$)-85.1 (s, 1F), −87.3 to 88.8 (m, 1F), −87.4 (s, 2F), −104.0 to −105.2 (m, 1F), −120.9 to −121.2 (m, 2F), −188.9 to −189.5 (m, 1F)

Having described our invention as related to the present embodiments, it is our intention that the invention not be limited by any of the details of the description, unless otherwise specified, but rather be construed broadly within its spirit and scope as set out in the accompanying claims.

What is claimed is:

1. A method of producing a fluorine-containing vinyl ether compound, comprising the step of:
fluorinating a compound represented by formula (I-1) or (I-2):

wherein R represents a straight-chain, branched-chain or cyclic alkyl group that may have a substituent and/or an unsaturated bond; $X_{11}$ represents a halogen atom other than a fluorine atom; $X_{12}$, $X_{13}$, and $X_{14}$ each independently represent a halogen atom; $X_{21}$ represents a halogen atom other than a fluorine atom; and $X_{22}$ and $X_{23}$ each independently represent a halogen atom, wherein the compound represented by formula (I-1) is obtained by chlorination of a compound represented by formula (IV-1):

wherein R represents a straight-chain, branched-chain or cyclic alkyl group that may have a substituent and/or an unsaturated bond; $X_{12}$, $X_{13}$, and $X_{14}$ each independently represent a halogen atom; and M represents a hydrogen atom, ammonium, or a metal.

2. The method of producing a fluorine-containing vinyl ether compound according to claim 1, wherein perfluorinating is conducted, in the fluorinating step.

3. The method of producing a fluorine-containing vinyl ether compound according to claim 1, which comprises the step of: dehalogenating a resultant fluorinated compound, after the fluorinating step.

4. The method of producing a fluorine-containing vinyl ether compound according to claim 1, wherein each of $X_{11}$ and $X_{21}$ in the compound represented by formula (I-1) or (I-2) is a chlorine atom.

5. The method of producing a fluorine-containing vinyl ether compound according to claim 1, which comprises the steps of: fluorinating the compound represented by formula (I-1), to give a compound represented by formula (II-1); and dehalogenating a compound represented by formula (II'-1), to give a compound represented by formula (III-1):

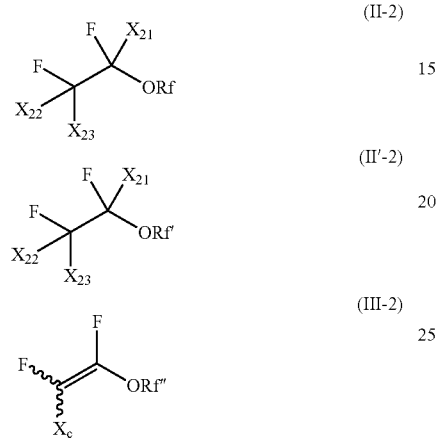

wherein, in formula (II-1), Rf represents a fluorine-containing alkyl group, in which at least one C—H bond in R in formula (I-1) is converted to a C—F bond; $X_{11}$ represents a halogen atom other than a fluorine atom; and $X_{12}$, $X_{13}$, and $X_{14}$ each independently represent a halogen atom; wherein, in formula (II'-1), Rf' has the same meaning as Rf in formula (II-1), or represents a group obtained by modification of a functional group of said Rf; $X_{11}$ represents a halogen atom other than a fluorine atom; and $X_{12}$, $X_{13}$, and $X_{14}$ each independently represent a halogen atom; and wherein, in formula (III-1), Rf'' has the same meaning as Rf' in formula (II'-1), or represents a group obtained by modification of said Rf' in the dehalogenation step; and Xa and Xb each represent a halogen atom derived from $X_{12}$, $X_{13}$ or $X_{14}$ in formula (II-1).

6. The method of producing a fluorine-containing vinyl ether compound according to claim 5, wherein $X_1$ represents a chlorine atom in formulae (I-1), (II-1) and (II'-1).

7. The method of producing a fluorine-containing vinyl ether compound according to claim 5, wherein any one of $X_{12}$, $X_{13}$, and $X_{14}$ is a chlorine atom, and the remaining two each are a fluorine atom in formulae (I-1), (II-1) and (II'-1); and Xa and Xb each are a fluorine atom in formula (III-1).

8. The method of producing a fluorine-containing vinyl ether compound according to claim 5, wherein any two of $X_{12}$, $X_{13}$, and $X_{14}$ each are a chlorine atom, and the remaining one is a fluorine atom in formulae (I-1), (II-1) and (II'-1); and one of Xa and Xb is a chlorine atom, and the other is a fluorine atom in formula (III-1).

9. The method of producing a fluorine-containing vinyl ether compound according to claim 5, wherein $X_{12}$, $X_{13}$, and $X_{14}$ each are a fluorine atom in formulae (I-1), (II-1) and (II'-1), and Xa and Xb each are a fluorine atom in formula (III-1).

10. The method of producing a fluorine-containing vinyl ether compound according to claim 5, wherein $X_{12}$, $X_{13}$, and $X_{14}$ each are a chlorine atom in formulae (I-1), (II-1) and (II'-1), and Xa and Xb each are a chlorine atom in formula (III-1).

11. The method of producing a fluorine-containing vinyl ether compound according to claim 1, which comprises the steps of: fluorinating the compound represented by formula (I-2), to give a compound represented by formula (II-2); and dehalogenating a compound represented by formula (II'-2), to give a compound represented by formula (III-2):

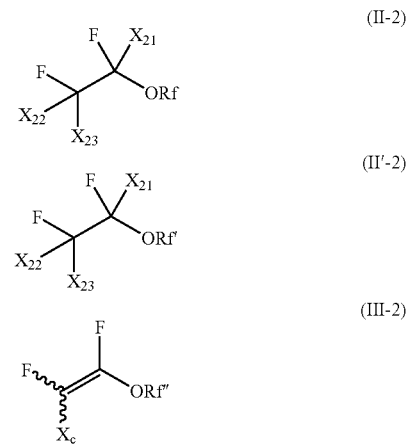

wherein, in formula (II-2), Rf represents a fluorine-containing alkyl group, in which at least one C—H bond of R in formula (I-2) is converted to a C—F bond; $X_{21}$ represents a halogen atom other than a fluorine atom; and $X_{22}$ and $X_{23}$ each independently represent a halogen atom; wherein, in formula (II'-2), $X_{21}$ represents a halogen atom other than a fluorine atom; $X_{22}$ and $X_{23}$ each independently represent a halogen atom; and Rf' has the same meaning as Rf in formula (II-2), or represents a group obtained by modification of a functional group of Rf; and wherein, in formula (III-2), Xc represents a halogen atom derived from $X_{22}$ or $X_{23}$, Rf'' has the same meaning as Rf' in formula (II'-2), or represents a group obtained by modification of the Rf' in the dehalogenation step.

12. The method of producing a fluorine-containing vinyl ether compound according to claim 11, wherein $X_{21}$ and $X_{22}$ each are a chlorine atom.

13. The method of producing a fluorine-containing vinyl ether compound according to claim 11, wherein $X_{23}$ is a fluorine atom.

14. The method of producing a fluorine-containing vinyl ether compound according to claim 11, wherein $X_{23}$ is a chlorine atom.

15. The method of producing a fluorine-containing vinyl ether compound according to claim 1, wherein R in the compound represented by formula (I-1) or (I-2) is a group represented by -L-CHClCH$_2$Cl, in which L represents a straight-chain, branched-chain or cyclic alkylene chain that may have a substituent and/or an unsaturated bond.

16. A compound represented by $CClF=CFOCF_2CF_2CF=CF_2$.

17. A compound represented by $CCl_2=CFOCF_2CF_2CF=CF_2$.

* * * * *

UNITED STATES PATENT AND TRADEMARK OFFICE
CERTIFICATE OF CORRECTION

PATENT NO. : 7,247,757 B2  Page 1 of 1
APPLICATION NO. : 11/242801
DATED : July 24, 2007
INVENTOR(S) : Takayuki Ito et al.

It is certified that error appears in the above-identified patent and that said Letters Patent is hereby corrected as shown below:

Title Page item 30 Add

--Foreign Application Priority Data--

--October 6, 2004, (JP) 2004-294224--

--May 9, 2005, (JP) 2005-136690--

Signed and Sealed this

Twentieth Day of May, 2008

JON W. DUDAS
*Director of the United States Patent and Trademark Office*